United States Patent
Zacharia

(10) Patent No.: US 11,172,916 B2
(45) Date of Patent: Nov. 16, 2021

(54) EYE SURGERY DEVICE

(71) Applicant: Peter Zacharia, Worcester, MA (US)

(72) Inventor: Peter Zacharia, Worcester, MA (US)

( * ) Notice: Subject to any disclaimer, the term of this patent is extended or adjusted under 35 U.S.C. 154(b) by 0 days.

(21) Appl. No.: 16/799,516

(22) Filed: Feb. 24, 2020

(65) Prior Publication Data
US 2020/0187930 A1    Jun. 18, 2020

Related U.S. Application Data

(63) Continuation of application No. PCT/US2018/047891, filed on Aug. 24, 2018.

(60) Provisional application No. 62/550,548, filed on Aug. 25, 2017.

(51) Int. Cl.
*A61B 17/02* (2006.01)
*A61B 90/30* (2016.01)

(52) U.S. Cl.
CPC ...... *A61B 17/0231* (2013.01); *A61B 17/0293* (2013.01); *A61B 90/30* (2016.02)

(58) Field of Classification Search
CPC .. A61B 17/0231; A61B 17/0293; A61B 90/30
USPC ...... 600/206, 233, 236, 245; 604/294; 606/4
See application file for complete search history.

(56) References Cited

U.S. PATENT DOCUMENTS

| | | | | |
|---|---|---|---|---|
| 5,267,553 | A * | 12/1993 | Graether | A61F 9/007 600/236 |
| 5,374,272 | A * | 12/1994 | Arpa | A61B 17/0231 600/236 |
| 6,162,172 | A * | 12/2000 | Cosgrove | A61B 17/0293 600/208 |
| 6,620,098 | B1 * | 9/2003 | Milverton | A61B 17/0231 600/236 |
| 8,496,583 | B1 * | 7/2013 | Reynard | A61B 17/0231 600/236 |
| 9,089,397 | B2 * | 7/2015 | Clarke | A61F 9/04 |
| 2003/0092970 | A1 * | 5/2003 | Lee | A61B 17/0231 600/236 |
| 2015/0359529 | A1 * | 12/2015 | Ganiban | A61B 90/30 600/203 |

FOREIGN PATENT DOCUMENTS

CA    2901850 A1 *  9/2014  ......... A61B 17/0293

* cited by examiner

*Primary Examiner* — Eduardo C Robert
*Assistant Examiner* — David C Comstock
(74) *Attorney, Agent, or Firm* — BrainSpark Associates, LLC

(57) ABSTRACT

Systems, devices and methods for dilating and/or expanding the iris of a patient's eye during eye surgery is disclosed, comprising an elastomeric ring made from biocompatible material having a groove formed therein for receiving and protecting the pupillary rim and iris, whereby, when the ring is inserted into the pupil of an eye of a patient, it mechanically dilates the pupil.

20 Claims, 14 Drawing Sheets

EYE SURGERY DEVICE

CROSS-REFERENCE TO RELATED APPLICATIONS

This application is a continuation application of Patent Cooperation Treaty (PCT) patent application PCT/US18/47891 entitled "EYE SURGERY DEVICE," filed Aug. 24, 2018, which in turn claims the benefit of U.S. Provisional Patent Application Ser. No. 62/550,548 entitled "Cataract Surgery Device," filed Aug. 25, 2017. The disclosures of each of these references is incorporated by reference herein in their entireties.

TECHNICAL FIELD

The invention relates to devices, systems and related surgical methods for dilating and/or expanding the pupil and stabilizing the iris of a patient's eye, for illuminating the retina and/or for directing flow of surgical irrigation fluid during eye surgery to facilitate and enhance the safety of eye surgery.

BACKGROUND OF THE INVENTION

Cataract surgery is one of the most commonly performed procedures in medicine, with millions of cataract surgery procedures performed annually throughout the world. In most eyes, cataract surgery is a relatively straight-forward procedure, with a low risk of complications. However, there are ocular anatomic characteristics which can increase the risk of complications during cataract surgery.

One anatomic characteristic which can increase the risk of complications during cataract surgery is a small, poorly dilating pupil. Good pupillary dilation is beneficial for numerous medical procedures, such as vitreoretinal surgery, anterior segment surgery, cataract surgery, especially phacoemulsification cataract surgery—to name but a few. In contrast, a small, poorly dilating pupil may make it difficult for the surgeon to visualize and/or access structures posterior to the iris, such as a cataract or vitreoretinal pathology. Where pharmacologic means fails to dilate a pupil sufficiently, the iris must typically be mechanically dilated to provide proper access.

A small, poorly dilating pupil can occur for a variety of reasons, including: (1) the presence of a condition called exfoliation syndrome, (2) the chronic use of miotic medications for glaucoma such as pilocarpine, (3) the destruction and stiffening of the iris sphincter that occurs in angle closure glaucoma, (4) the formation of iris to lens adhesions called synechiae in eyes with uveitis and other conditions, (5) the use of certain systemic medications such as alpha-1 receptor antagonists, and/or (6) a variety of other conditions.

For example, one characteristic which can place an eye at higher than typical risk for complications during cataract surgery is relaxation or atrophy of the dilator muscle within the iris, which can occur with chronic use of alpha-1 receptor antagonists, one example of which is tamsulosin—a medication used for treatment of urinary retention in patients with benign prostatic hyperplasia. This medication can cause both a small and poorly dilating pupil and also floppy iris behavior during cataract surgery, termed Intraoperative Floppy Iris Syndrome (IFIS). IFIS manifests as a billowing of the iris and can occur when irrigation fluid, which fills the eye during cataract surgery, is directed behind the iris. This can cause the iris to prolapse or herniate through the cataract surgery incision(s), resulting in not only damage to the iris, but also causing incisions to gape open, resulting in excessive outflow of irrigation fluid from the eye and shallowing or collapsing of the anterior chamber space within the eyeball. When there is shallowing of the anterior chamber, the area anterior to the iris and the cataractous lens, there is less space available for instrumentation within the eye and for the process of emulsifying and removing the cataract material. This makes cataract surgery by phacoemulsification more difficult and increases the risk of damage to ocular structures such as the capsular bag around the cataract, the iris, and the cornea.

If an operation is performed through a small pupil, it can lead to severe trauma to the iris stroma and damage to the iris sphincter, potentially resulting in permanent iris distortion and disabling glare. Additionally, poor visualization of the procedure may lead to a small capsulorrhexis (which may result in a contraction syndrome requiring additional procedures to perforate the contracted capsule), zonular dehiscence, capsular rupture, vitreous loss leading to permanent decreased vision, lens material in the posterior segment requiring retinal surgery for removal, retained cortical material and/or prolonged surgical times. Each of these complications is potentially avoidable by fixed dilation of the pupil. Although mydriatic drugs are preferred for dilating the pupils, in many patients these drugs are ineffective because of the patient's ocular pathologic characteristics—including use of certain medications as discussed above, exfoliation syndrome, iris to lens synechiae, etc. Several solutions, both demolitive and conservative, have been attempted.

The demolitive measures, such as sector iridectomies and sphincterotomies, for example, both suffer from the same shortcomings—each can potentially permanently deprive the patient of normal pupillary kinetics. For example, both of these interventions may lead to permanent dilation and disabling glare.

Among more conservative measures, pupillary stretching using two intraocular hook-like instruments was often employed before the development of devices which held and maintained a dilated pupil during surgery. However, this technique can also result in tearing of the pupillary sphincter with loss of pupillary function, permanent mydriasis, or irregular pupil postoperatively. The effect of stretching is often not sustained with loss of dilation during surgery. In the case of a small pupil in patients using alpha-1-receptor antagonists who develop an intraoperative floppy iris syndrome, stretching the pupil will not only fail to stabilize the iris, but there will be a persistent billowing and tendency to prolapse of iris tissue from surgical incisions—and stretching often exacerbates this floppy iris and/or iris prolapse behavior.

There are a number of commercially available mechanical iris "stretching" devices, including variations of ring-like structures which desirably directly expand the pupil by pushing outward on the iris at one or more locations to expand the pupil. These devices remain within the eye to maintain a dilated pupil during surgery and are removed at the completion of the procedure. Some of these devices are discontinuous rings which require multiple adjustments for positioning, while others are continuous rings with self-retaining features that attempt to hold the pupil open at 4 to 6 points, which can create "notching" of the iris sphincter at the points of contact. These devices include (1) The Malyugin ring, (2) the Visitec I-Ring, (3) the Bhattacharjee pupil expansion ring, (4) the Graether 2000 pupil expander, and (5) the Morcher Pupil dilator. Unfortunately, all of these devices require multiple steps for insertion, proper placement, proper positioning and expansion of the pupil. Moreover, none of these devices block peripheral iris tissue from prolapsing into the surgical incisions. Other existing devices can be inserted through and held within supplemental eye incisions, but these devices dilate in a square or diamond-like fashion and require multiple additional incisions for placement to dilate the pupil. Examples of these are the Assia pupil expanders and the FCI Ophthalmics Polypropylene Iris hooks.

A more recently developed device—the Clarke horseshoe dilator—expands the pupil and provides partial protection to the iris with a 2 mm rim which lies over the iris after insertion and 4 underlying tabs which are positioned posterior to the iris to desirably retain the device during surgery and dilate the pupil. While the Clarke horseshoe provides some overlap onto the iris, it does not cover enough of the iris to prevent iris prolapse and is a discontinuous ring, which would allow herniation of iris tissue through the discontinuity and prolapse of the herniated iris from the surgical incision.

In addition, current methods of illuminating the retina during surgery on the vitreous and retina (vitrectomy surgery or vitreo-retinal surgery) involve placing a light source through a pars plana scleral incision to illuminate the surgical field while other pars plana incisions are made for insertion of other surgical tools such a forceps, scissors or picks. Small pars plana incisions for vitrectomy surgery allow for maintenance of the structure of the eye and a controlled environment during surgery. Pars plana scleral incisions have been getting smaller—from the 20 gauge incisions initially used for small incision pars plana vitrectomy surgery in the 1970s to more recent incisions allowing smaller gauge instrumentation as narrow as 25 and 27 gauge instruments. Narrower gauge instrumentation is desirable to reduce the chance of leakage from the incisions after the surgical procedure is complete and instrumentation is removed from the scleral incisions. Use of narrower gauge instruments also has allowed for sutureless vitrectomy surgery, for which no sutures are required, to close the smaller bore incisions at the completion of surgery. Smaller incisions have also allowed for less disruption of the conjunctiva overlying the sclera.

With smaller gauge vitrectomy instrumentation, however, comes light sources with smaller diameters typically providing less illumination of the retina than larger gauge light sources. Two more recent developments have attempted to "make up" for this reduction in light produced by smaller gauge light instruments. First, newer light sources, including Xenon light. mercury vapor and/or LED (light emitting diode) light sources have allowed for improved light output over older halogen light sources. Second, chandelier light sources have been employed during retina surgery in an attempt to illuminate the retina using a wider-angle illumination probe placed further from the retina and closer to the incision, desirably resulting in illumination of more of the retina and surgical field than non-chandelier light instruments. These chandelier light sources also have the advantage of being self-retaining within the incision, allowing the surgeon to have an extra hand free to manipulate instrumentation during surgery. Chandelier lighting systems are available in single chandelier sources and dual fiber systems. With single fiber systems, retinal surgical instruments positioned between the light source and the retina often create shadows that fall upon the retina, interfering with adequate illumination. Dual fiber systems attempt to make up for this shortfall with an additional light source providing illumination from a different direction—but these systems require an additional incision to be made. Single fiber chandelier systems may also require repositioning of the light source to illuminate a section of the retina not previously illuminated by the original positioning. Glare can also be another problem which affects a chandelier lighting system with the diffuse light source posterior to the lens plane, especially in a pseudophakic eye with gas condensation on the posterior surface of the intraocular lens after fluid-air exchange during retinal detachment surgery.

Some alternatives to using separate lighting instruments to illuminate the retina during surgery are light sources incorporated into the surgical instrumentation for vitreoretinal surgery, such as retinal picks and forceps with attached lighting. These instruments attempt to allow the surgeon to keep the second hand free to manipulate instrumentation while obviating the need for a separate pars plana incision for a light source, but this approach will only illuminate the portion of the retina directly adjacent to the instruments, and also greatly increases the complexity and cost of the surgical tools.

It is also a concern that excessive and prolonged light exposure during vitreoretinal surgery can damage the retina, and this phototoxicity can be exacerbated when light sources have greater light output or are placed closer to the retina. More intense or prolonged lighting will shorten the amount of time a surgeon can use supplemental light sources to complete a procedure without causing light damage to the retina. Placing the light source farther from the retina can allow for significantly longer surgical time by increasing the threshold time for retinal phototoxicity, since the risk is typically reduced with a more distant light source. Another factor which can exacerbate light induced retinal phototoxicity during surgery is the use of shorter wavelengths of light. Light sources with higher wavelength peaks, such as mercury vapor light sources and/or use of filters to filter out shorter wavelengths in the ultraviolet and blue light range, desirably reduce phototoxicity caused by shorter wavelengths.

With respect to retinal illumination during vitreoretinal surgery, currently available devices placed within the eye for illumination of the retina require a separate pars plana scleral incision, and these devices illuminate in a focal manner and not the entire retina at once. Additional scleral incisions often require suturing and a focally directed light source will illuminate only the portion of retina at which it is directed requiring movement of the light source during surgery.

Surgeons also often perform gonioscopy, which allows them to visualize the anterior chamber angle, pars plana, and ciliary processes during eye surgery (either with a mirrored lens or a prismatic lens). This procedure is accomplished during surgery on the anterior chamber angle, the pars plana, or ciliary processes with use of a either a hand held gonioscopy lens with mirror incorporated or a gonioprism. Either of these are placed on the corneal surface to allow visualization of these structures during surgery. Current devices require the use of one of the surgeon's hands to hold the gonioscopy lens or prism in place, leaving only one hand for use of other instrumentation.

During many surgical procedures, irrigation of the anterior chamber of the eye is typically necessary for the purpose of maintaining the anterior chamber space and removing surgical debris and blood during anterior segment surgery including phacoemulsification cataract surgery. This can be accomplished using a coaxial irrigation sleeve attached to the phacoemulisification or aspiration instrument or by use of a separate irrigation tip placed through a separate incision. The latter approach with separated irrigation may require holding with the surgeon's second hand or may be self-retained within a limbal incision. A separated irrigation tip will also typically require creation of a second incision and/or use of the second hand, so that the second hand will be occupied and unable to use another surgical instrument. However, use of a separate irrigation source has the advantage of being able to direct and position irrigation independently of the position of or movement of the phacoemulsification or aspiration tip. This can be important in certain surgical situations, especially when the iris has a greater tendency to prolapse from the surgical incision such as with use of alpha adrenergic inhibitors, the condition known as intraoperative floppy iris syndrome (IFIS). In IFIS situations, irrigation fluid directed behind the iris will cause billowing of the iris and prolapse into the surgical incision. A separated irrigation source keeping irrigation directed above the iris can reduce the tendency for this to occur. Irrigation coaxial with an aspiration tip will often make this more likely to occur, especially when the aspiration tip must be positioned below the iris plane such as when a phacoemulsification tip reaches into the capsular bag to remove a cataract fragment or when a cortical aspiration tip reaches into the capsular bag during cataract surgery to remove lens cortex.

BRIEF SUMMARY OF THE INVENTION

The present invention includes the realization of a need in the art for devices, systems and procedures for reliably dilating the iris of a patient during a surgical procedure and maintaining dilation, while at the same time protecting the iris from damage due to sharp surfaces, unbalanced fluid pressures, excessive dilation forces and/or uneven or point-pressure on various portions of the iris and/or related anatomy. Additional embodiments of the present invention include the recognition of a need for improved surgical illumination within the eye, a need for improved systems for examining various features of the eye either directly or via reflective, magnifying and/or other surfaces and/or the need for improved irrigation systems for use during surgical procedures of the eye.

In this description, unless otherwise specified anterior and posterior refer to the position of the device within the eye, anterior meaning in the direction of the cornea or the front of the eye and posterior meaning in the direction of the retina or the back of the eye.

In various embodiments, a desired amount of iris dilation and degree of dilation force(s) can be provided by a ring-shaped implantable iris dilation device comprising a pair of concentric generally flat rings connected together via a continuous circular central rim. The device can include a larger, anterior ring section and a smaller posterior ring section, the two sections spaced apart and connected together by a central rim section. In at least one exemplary embodiment, the anterior ring section, posterior ring section and central rim section can include perforations or pores extending completely through the respective sections, which can desirably provide one or more fluid flowpaths to allow for pressure equalization and/or normalization between the anterior and posterior portions of the eye during surgical procedures. This device will desirably mechanically dilate the pupil when pharmacologic or other means to do so are insufficient, allow pressure equalization between various sections of the eye and also desirably suppress and/or eliminate iris billowing and/or hold back iris tissue to prevent iris prolapse from incisions in eyes suffering from IFIS and/or eyes which have a tendency to have iris prolapse from the surgical incision during intraocular surgery such as cataract surgery.

The present invention discloses devices that are adapted to easily, safely and reliably engage and mechanically dilate the pupillary rim of an iris. In various embodiments, the device can comprise a ring made of biocompatible elastic material, having a generally J-shaped, U-shaped and/or C-shaped circumferential groove or channel formed therein, which is adapted to receive and protect the pupillary rim. The central groove desirably divides the device into an anterior flange portion, a connecting central wall or rim portion and a posterior flange portion.

During a surgical procedure, at least one exemplary embodiment of an iris dilation device (desirably formed from flexible and/or foldable materials) can be introduced into the eye in a compressed and/or folded state (i.e., through a small incision, such as an incision currently made for eye surgery such as cataract surgery). This device can be introduced into the anterior eye chamber and desirably positioned proximate to the iris to capture some or all of a pupillary margin of the iris tissue of the iris between the anterior and posterior ring section, with the posterior ring section desirably incorporating a tapered or angled inner surface in some embodiments, which allows the posterior ring to potentially slide along and/or abut portions of the iris to desirably progressively urge and/or position the iris within the central rim section, and further facilitate iris dilation as the dilation device expands and/or unfolds in a desired manner (i.e., as the device is permitted to return to an undeformed shape). As the dilation ring expands radially outward, the force against the pupillary rim desirably urges it to enter and/or maintain position within the central groove until the rim is fully received therein. Depending upon the size of and/or the restoration force of the ring employed, the expansion can continue until the ring has reached its fully undeformed shape and/or the force of the central rim against the pupillary rim reaches a desired level of compression against the pupillary rim (which may be less than a full restoration of the dilation device's undeformed shape). Because the ring desirably distributes the dilation force equally over the entire pupillary rim, the pupillary rim and/or other iris structures are unlikely to become damaged and/or unduly stressed in one or more discrete locations during the surgical procedure, which should allow the pupil to resume its non-dilated size and shape upon removal of the dilation device (i.e., at the completion of the surgical procedure).

In at least one exemplary embodiment, the dilation device can include an anterior ring of sufficient diameter to cover and protect a majority of and/or the entire area of the iris and block a significant amount of the iris tissue from billowing and herniating or prolapsing into incisions made for cataract surgery. The anterior ring can desirably have a central opening through which structures posterior to the iris, such as the cataractous lens, can be visualized and accessed. Both the outer and/or inner circumference of the anterior ring can be made more rigid than the material between the borders, if required and/or desired for structural support, or various portions of the outer and/or inner circumference can be made more or less rigid than each other and/or than various portions thereof. In various embodiments, the anterior ring can incorporate a plurality of positioning holes formed therethrough to facilitate maneuvering the ring within the eye and/or safe removal of the device from the eye at the completion of surgery, as well as allow fluid flow therethrough for pressure relief and/or equalization during the surgical procedure. Removal of the distraction device can be facilitated by a hole of sufficient size to allow grasping and engagement with a surgical hook such as a Sinskey or collar-button hook. By engaging the hole in the anterior ring which is diametrically opposite from the surgical incision, the posterior ring can be lifted above the pupil at the point in the circumference opposite the incision such that the posterior ring will gradually and/or progressively disengage with the pupillary border and rise above the border as the assembly is pulled anterior to the iris and peeled back towards the incision (which can include posterior bending and/or deflection of the posterior flange, in various embodiments). A skilled surgeon will desirably use the necessary caution to make certain that the entire posterior ring is fully disengaged from the iris as the ring assembly is peeled back and pulled out of the surgical incision to avoid tearing of the iris at its insertion into the ciliary body. The compressibility and/or foldability of the ring assembly will desirably allow easy travel through the surgical incision.

In various additional embodiments, similar alternative design, material and/or structural considerations could be utilized for the posterior ring and/or central section, if desired.

In some embodiments, the anterior ring could incorporate two or more suture guide slits and/or openings, which could be arranged, positioned and oriented to facilitate iris suture fixation of an intraocular lens during complicated cataract surgery cases or secondary intraocular lens implant cases (including cases in which the eye may have been left aphakic during initial cataract surgery because of a complication, and surgery is being done to implant and intraocular lens secondarily). Where this feature is utilized, an intraocular lens optic can be placed into the anterior chamber of the eye such that it approximates or rests on the larger ring of the device, with the haptics desirably tucked posteriorly behind both the device and the iris. At the surgeon's option, positioning and rotation of the intraocular lens with respect to the device in preparation for suture fixation could be planned such that the haptics would be directly posterior to two or more suture guide slits, with the slits guiding and/or identifying ideal suture placement, both by indicating/guiding the initial penetration of the suture needle going posteriorly through the iris and also indicating/guiding the second penetration of the suture needle back through the iris back into the anterior chamber (after engaging the lens haptic). In cases when the device may be used to facilitate suture fixation, it may sometimes be more desirous to excise 2 or more arcs from the smaller posterior ring of the device, where the arcs can be aligned with the suture fixation slits, in an attempt to prevent the intraocular lens haptics from being directed more posteriorly by the presence of the dilation device. Excision of these two arcs could be preplanned (and/or incorporated into the device preoperatively), or the arcs could be created operatively by the surgeon prior to placing the ring device within the eye, when it is known that the iris suture fixation of an intraocular lens may be performed. Alternatively, the device may be made available with the arcs already present as optional features in construction of the device for surgeons who wish to use a device pre-configured for use during iris-suture fixation of an intraocular lens.

In various embodiments, the posterior ring will also have a central opening, which can be of the same or different diameter as the larger anterior ring, and which will desirably be generally aligned with the central opening of the larger ring (although alternative embodiments having smaller and/or larger diameters for the posterior ring and/or non-aligned central openings are contemplated herein). The outer diameter of the posterior ring can be smaller than that of anterior ring, if desired, but will desirably be large enough to rest behind the edge of the pupil and engage the iris pupillary border and prevent disengagement during dilation and the surgical procedure. In various embodiments, the reduced radial width of the posterior ring (and the angled posterior flange formed therein) as compared to the larger anterior ring (and the anterior flange respectively formed therein) can be highly beneficial for placement, operation and/or removal of the dilation device, in that the anterior flange can protect and retain most or all of the iris tissue, while the angled posterior flange aids in guiding the pupillary rim into the groove during insertion of the ring. Further, the anterior flange can serves to prevent trauma to the iris sphincter and stroma and prevent iris prolapse from the surgical incision during phacoemulsification. In addition, when the dilation device is to be removed, the angled posterior flange in some embodiments can easily deform or "collapse" laterally, which can cause the anterior and/or posterior flanges to deform and/or "flatten" to some degree and "release" from the iris (and also desirably presents a smooth, generally rounded surface to the iris during such removal operation).

During use, dilation of the iris is desirably maintained by the continuous circular rim which joins the two flat rings and connects to the inner rim of each ring. If desired, the smaller posterior ring can feature one or more partial thickness (i.e., with respect to the antero-posterior dimension) notches in the anterior and/or posterior facing surface of the posterior ring, which can span the width of the ring from the outer to the inner border. These notches may be desired to allow fluids to flow from the inside of the smaller ring to the surrounding space, and thereby prevent a valve-like effect or lens-ring "block," where the flow of irrigation fluid during cataract surgery might be restricted and result in the lens/device complex being pushed and/or urged posteriorly by fluid pressures. To achieve similar functionality, the device may be alternatively constructed with full thickness fenestrations and/or openings in the central connecting rim which could also allow for fluid flow through various portions of the device to desirably prevent a lens-ring "block".

In various embodiments, the insertion of the dilation device into the anterior chamber can be facilitated by an injector device (not shown) having a tip which allows introduction of the device into the eye through a small incision made for eye surgery. The dilation device can be folded and/or rolled within the injector, with the tip allowing the device to unfold and/or unroll when it exits the tip of the injector (after introduction into the eye). If desired, the injection tip can include alignment and/or indicating features for positioning the dilation device relative to the iris in a desired location and/or orientation, including the potential for a guide or other type of tip that engages and/or aligns with some portions of the iris during the deployment procedure.

By virtue of the foregoing and detailed description below, there is thus provided devices and surgical methods for quickly, easily and safely dilating the pupil of an eye during surgical procedures. These and other objects and advantages of the present invention shall be apparent from the accompanying drawings and the descriptions thereof.

One additional feature which could be incorporated into various embodiments of the disclosed device can be a light source placed on and/or within the posterior ring of the device, which can include an element which provides illumination as well as elements which provide energy to the light source, such as a battery and/or loop/ring antenna. These embodiments would desirably provide a uniform illumination of the retina and vitreous for vitreoretinal procedures and procedures involving the ciliary body such as endocyclophotocoagulation procedures. In various embodiments, the illumination device would desirably be held in place by iris fixation of the device and could be used both in phakic and pseudophakic eyes.

BRIEF DESCRIPTION OF THE SEVERAL VIEWS OF THE DRAWINGS

The foregoing and other objects, aspects, features, and advantages of embodiments will become more apparent and may be better understood by referring to the following description, taken in conjunction with the accompanying drawings.

DETAILED DESCRIPTION OF THE INVENTION

Figure 1:
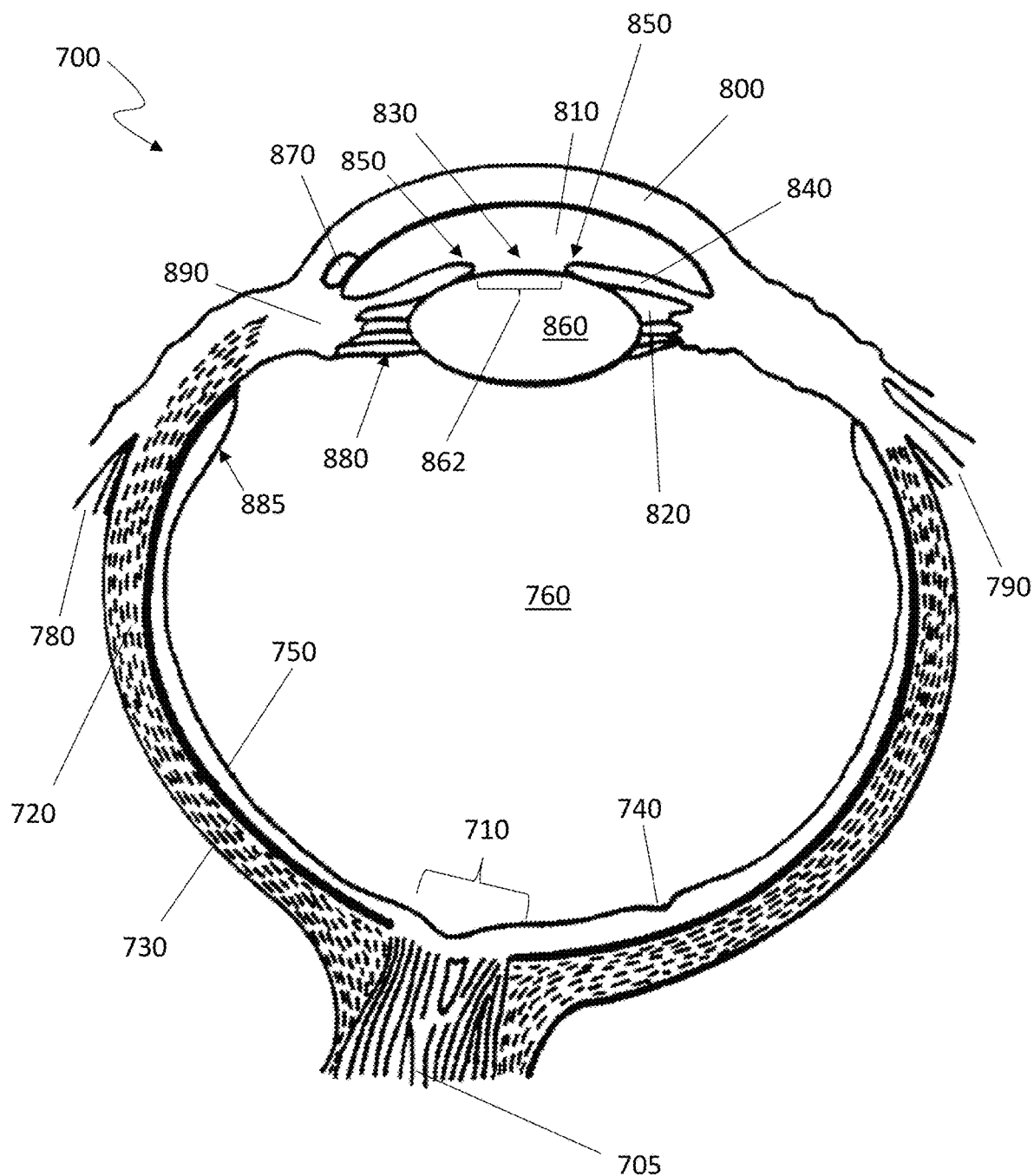
FIG. 1 depicts a cross-sectional view of a typical human eye.
Figure 2:
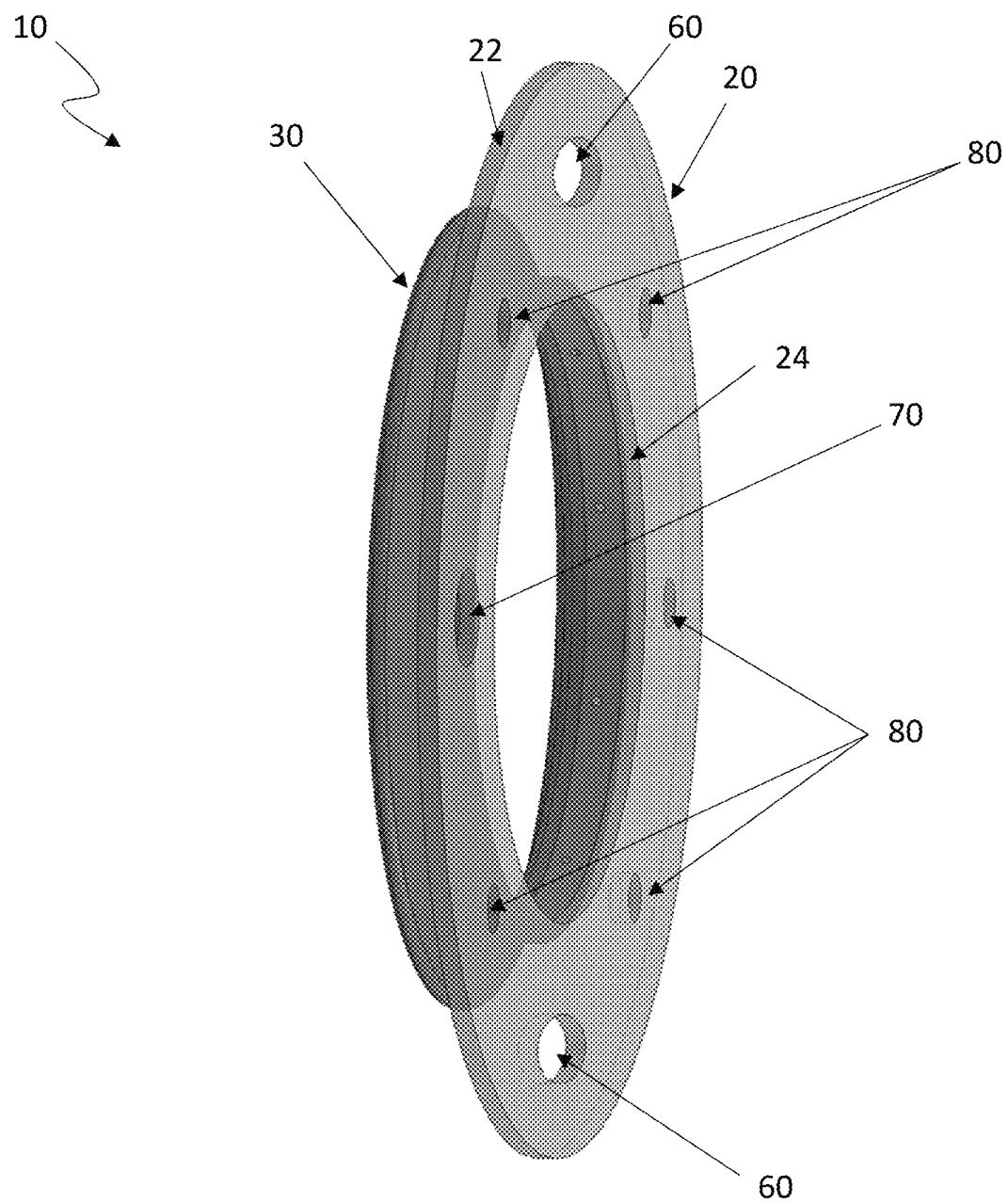
FIG. 2 through 5 depict various view of one exemplary embodiment of a pupillary dilation device.

FIG. 1 depicts a cross-sectional view of a typical human eye 700, showing various posterior structures of the eye including the optic nerve 705, an optic disc 710, the choroid 730, the macula lutea 740 and the retina 750, with the vitreous body 760 (filled with vitreous humor) occupying much of the central aspect of the eye, and the sclera 720 (or white of the eye) forming the opaque, fibrous protective outer layer of the eye. In addition, various anterior eye structures depicted include the cornea 800, an anterior chamber 810 (filled with aqueous humor) and a posterior chamber 820 (which together comprise the Anterior Cavity), the pupil 830, the iris 840 and pupillary rim 850, a lens 860, the Canal of Schlemm 870, zonules 880, the pars plana 885 and the ciliary body 890, with the medial rectus muscle 780 and the lateral rectus muscle 790 also shown (which are two of the six muscles that control movements of the eye).

During some surgical procedures involving the eye, such as during cataract surgery, access to various internal eye structures may be obtained through one or more incisions made in and/or at the borders of the cornea and/or sclera. Once access within the anterior chamber of the eye has been obtained, other internal structures further within the eye may be accessed through the pupil, which is the aperture in the iris. In many cases, a pupil can be dilated (i.e., enlarged) pharmacologically to a desired size to provide adequate surgical access or for other reasons, but in some cases this iris dilation will be insufficient and/or ineffective, and thus physical dilation of the iris using a pupillary dilation device may become necessary.

Figure 3:
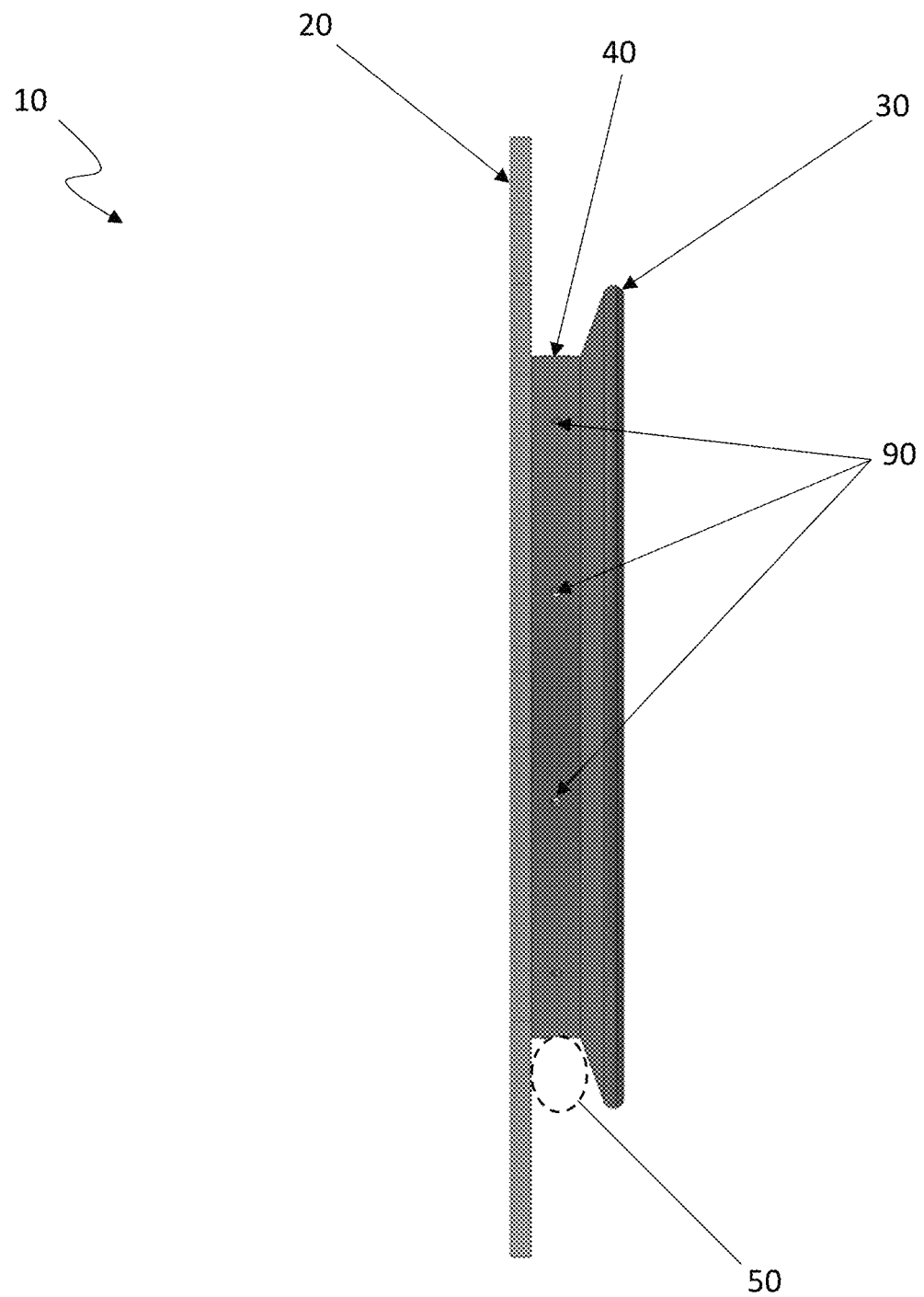

As best seen in FIGS. 2 through 5, one exemplary embodiment of a pupillary dilation device 10 can comprise an anterior ring section 20, a posterior ring section 30 and a central rim section 40. As best seen in FIG. 3, these three sections desirably outline a generally trapezoidal, J-shaped or U-shaped cross section, forming a cup or groove 50, with the anterior ring section 20 being somewhat larger in diameter than the posterior ring section 30 (i.e., the anterior radial flange is somewhat larger the posterior radial flange). Desirably, the groove is sized and configured to accommodate the pupillary rim 850 and iris 840 of the eye (see FIG. 6), which will desirably allow the groove to contain these structures as the device 10 expands and mechanically dilates the iris.

In one embodiment, the thicknesses of each of the anterior and posterior ring sections can be approximately 0.2 mm. If desired, the central connecting ring could also be 0.2 mm thick, while the height or gap between the anterior and posterior rings could be 0.5 mm to accommodate the thickness of the iris at the pupillary border. The larger anterior ring section 20 of the dilation device 10 can be made in various outer diameters, such as 8 mm, 9 mm, 10 mm, 11 mm, 12 mm, 13 mm, 14 mm, 15 mm, 16 mm, 17 mm (and so on), where the 12 mm size may be typically used with most average patients, and the rest of the sizes available to accommodate patients of atypical anatomical size and/or configuration and/or for various other surgical procedure types. In one exemplary embodiment, a 12 mm outer diameter and 6.3 mm inner diameter for the anterior section may be most preferred, as this size is likely to best cover most of the iris in a wide variety of patient eyes and also provide sufficient dilation for surgical needs. Desirably, the coverage of a significant amount of peripheral iris (which may include covering as much peripheral iris as possible) will help to prevent prolapse of the iris tissues into the incision(s). If desired the surgeon will select, for a specific patient, an appropriate size and/or size range for the device, which may be estimated by measuring the diameter of the cornea for the specific patient undergoing eye surgery—also called the white-to-white distance. Desirably, the anterior ring kit can include distraction devices available in a range of sizes corresponding to the distribution of sizes of eyes in the population and an operative estimation of the size required for a given eye would be based on the corneal diameter to estimate the size of ring required to cover the iris during surgery.

In the disclosed embodiment, the dilation device 10 desirably has a central opening 15 of approximately 6.3 mm in diameter, although this interior size could be increased and/or decreased based on patient anatomical considerations and/or surgical access requirements, including inner diameters of approximately 4 mm, 5 mm, 6 mm, 7 mm, 8 mm, 9 mm, 10 mm, 11 mm, 12 mm, 13 mm and/or others.

The larger anterior ring section 20 can comprise a clear transparent flexible material, such as acrylic and/or silicone, of about 0.1 mm to 0.3 mm in thickness or "width" (depending upon the material used and the inclusion of any supporting and/or shape memory materials). The selection of the appropriate material used as well as thickness of the ring section can be important so as to allow for the volume of the device when folded or rolled to be sufficiently small to fit through a surgical incision for insertion into the eye. Optionally, the outer and/or inner borders 22 and 24 of the anterior ring section 20 may contain and/or be bounded by a relatively more rigid (but still flexible) skeletal element, if necessary to give structural support, which may include flexible structures comprising shape memory materials (which may be attached to and/or embedded within material of the anterior ring section material, such as during injection molding). In various embodiments, the larger anterior ring section 20 and/or other sections of the device 10 may include a variety of "shape memory" features, which would desirably allow the device 10 to unfold and regain its normal shape slowly over a period of 2 to 3 (or more) seconds, since a quick recovery of shape in a fast spring-like fashion within the surgical field may be less desirable, in that it might damage the iris, ciliary body and/or cornea during unfolding.

In one alternative embodiment, the peripheral portion of the anterior ring may be constructed with a reflective anterior surface, which would desirably facilitate visualization of the anterior chamber angle without the need to use a gonioscopy lens placed on the cornea. During examinations of the eye or during glaucoma surgery, the anterior chamber drainage angle cannot typically be visualized without the use of a mirror or prism, which is currently incorporated within a lens held on the surface of the cornea called a gonioscopy lens. This alternative embodiment of the device with a reflective anterior surface could desirably be used in anterior chamber angle procedures such as angle procedures for treatment of glaucoma. This embodiment can help keep the second hand of the surgeon free, so that the surgeon can use the second hand to grasp another instrument, expanding the range of possibilities for surgical procedures. Alternatively, the anterior ring could be constructed of a clear material, with the periphery incorporating a mirrored surface to allow visualization of the anterior chamber angle while the transparency of the more central section allows visualization of the posterior ring as it engages the pupillary border.

In one preferred embodiment, the smaller posterior ring section 30 can have an inner diameter of approximately 6.3 mm, with an outer diameter of approximately 7.5 to 7.9 mm, such that approximately 0.6 mm of the ring 30 extends outward (i.e., away from the central rim section 40, which could desirably have a thickness of approximately 0.2 mm to form a posterior "flange") which is desirably of sufficient width to contain and/or engage with the iris. Desirably, the posterior flange can be sloped or tapered "away" from the central rim and/or the anterior flange to some degree, which in the disclosed embodiment is a width (of the sloped lip of the posterior ring section) of approximately 0.6 mm. An inner border of the posterior ring section 30 is desirably connected to an inner border of the anterior ring section 20 by the central rim section 40, which in various embodiments may be approximately 0.5 mm high and 0.2 mm thick, which desirably creates a gap of approximately 0.5 mm for the groove between the anterior and posterior ring section 20 and 30 of sufficient dimension to allow the pupillary border to be captured and retained between the anterior and posterior ring section.

Figure 4:
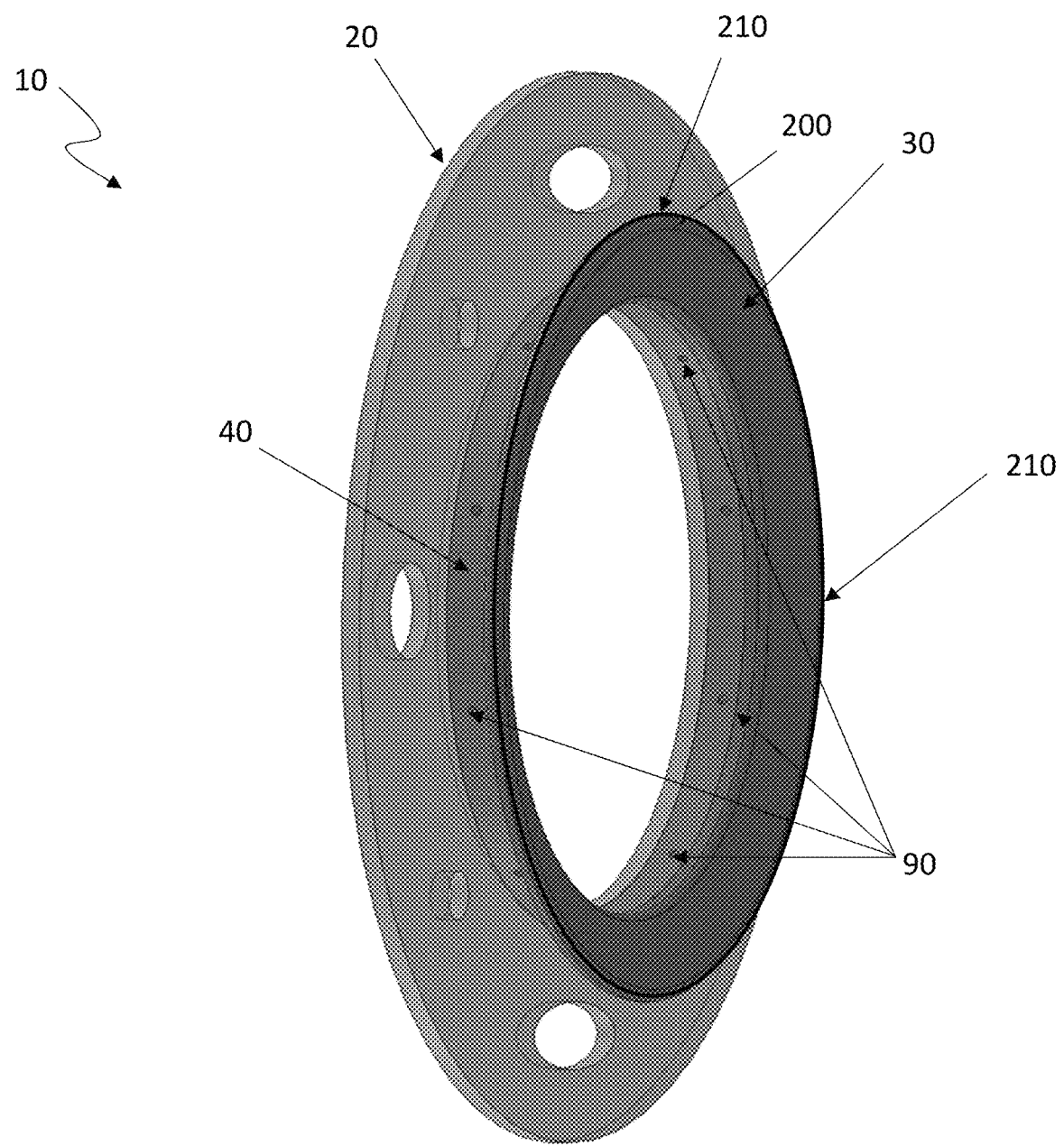
Figure 5:
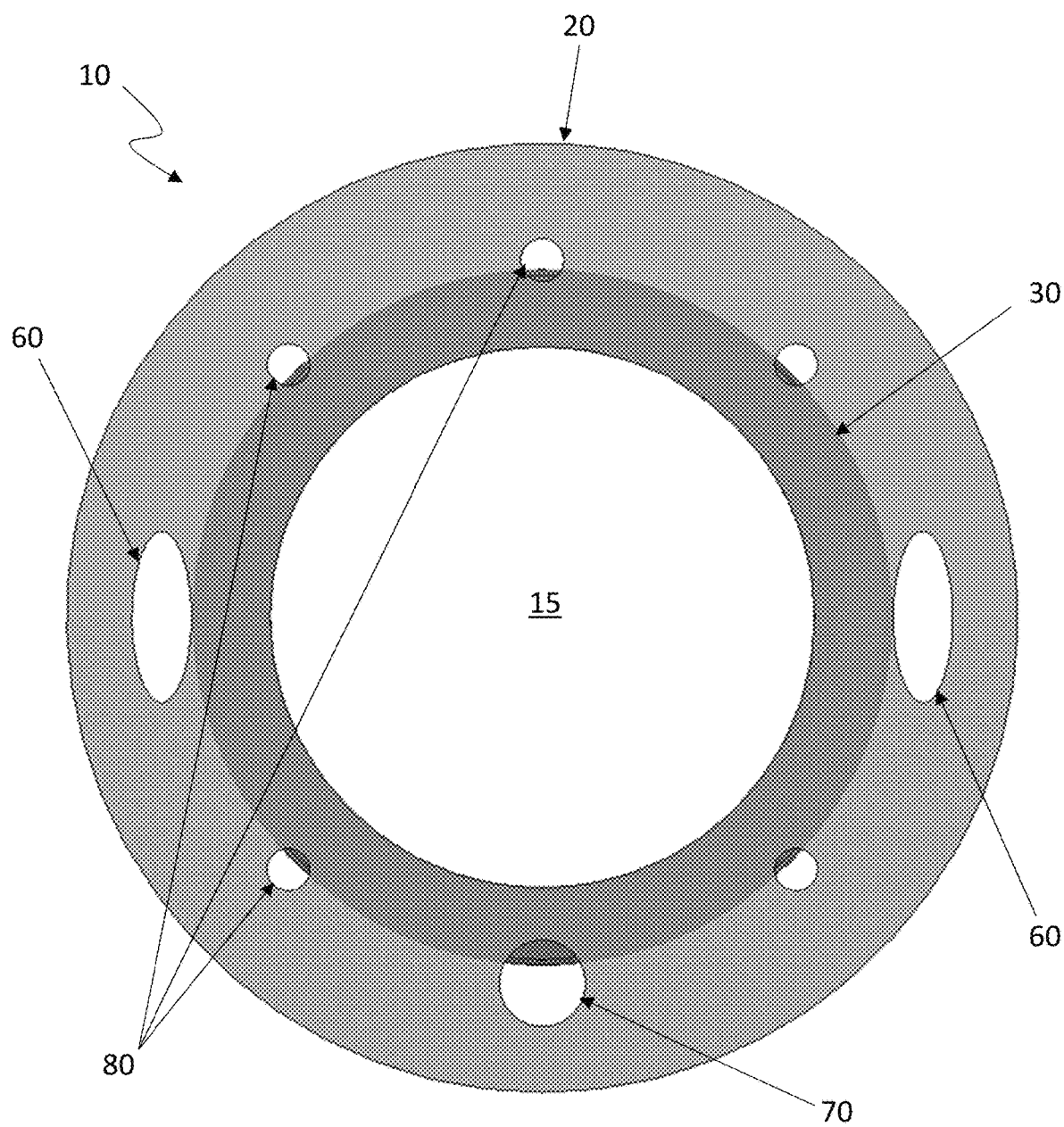

As previously noted, various embodiments will include an anterior ring section 20 comprising a transparent or translucent material, which can allow and/or facilitate visualization of the posterior ring section 30 through the anterior section at various points during deployment, dilation and/or device removal. In various embodiments, a black or darkly shaded border highlighting the posterior ring outer circumference may be incorporated to desirably enhance visualization of the posterior ring when unfolding during insertion into the eye with the injector, which can facilitate placement of the posterior ring under the iris as it exits the injector and/or make it easier to see when the posterior ring has engaged the pupillary border (and also when the posterior ring disengages the pupillary border during device removal). The darkly shaded border of the outer circumference of the posterior ring, as viewed through the transparent anterior ring, would desirably be hidden by the iris when it is posterior to the iris. As best seen in FIG. 4, the peripheral border 200 of the posterior ring section 30 could incorporate a black or white or other color pigmented strip 210 which is desirably visible from the anterior aspect of the device and which also enhances the surgeon's ability to determine if the pupillary rim 850 and/or iris 840 of the eye are properly positioned within the groove 50 when the device is fully unfolded (as well as during the surgical procedure and/or during device removal). When properly positioned in the groove 50, the pupillary rim 850 and/or iris 840 will desirably occlude the indicator strip 210, with the strip 210 only visible when the iris is not positioned within the groove 50. Desirably, the colored line makes it easier for the surgeon to visualize engagement of the iris as the pigmented line disappears beneath the iris. This pigmented line as well as the transparency of the anterior ring will also allow for visualization during removal of the device from the anterior chamber of the eye to allow the surgeon to be certain that the posterior ring does not snag and pull the iris during removal of the device.

In at least one alternative embodiment, an illumination mechanism could be incorporated onto and/or into the smaller posterior ring, such as a light emitting diode filament with an energy source such as a battery or incorporated device allowing electromagnetic energy transfer and/or induction coupling, which would serve to illuminate the intraocular space one or both in the anterior and/or posterior and/or lateral directions, which could include illumination of the posterior segment including vitreous and retina as well as the ciliary body. This arrangement could facilitate visualization of these structures during vitreoretinal surgery or procedures involving the ciliary body such as ciliary body photocoagulation procedures. The light source, when in apposition to the anterior lens capsule, may in some cases enhance visualization of the anterior capsule obviating the need for capsular dyes in cases when the cataract is very opaque. In various embodiments, retinal illumination during exam or surgery on the retina can be provided by the device, which can be placed in the anterior portion of the eye (i.e., anterior or posterior chamber, anterior to pars plana) and not requiring a pars plana incision, with the device optionally including a mechanism for being self-retained, and which may include either an energy source or a mechanism for wireless and/or non-contact energy transfer, and which may optionally include one or more insulating surface(s) to prevent heat generated by the light source and/or other components from causing damage to intraocular structures.

By placing an illumination mechanism on/in the posterior ring, the entire posterior part of the eye, including retina and vitreous, can be illuminated uniformly. This would make shadowing from vitreoretinal surgical instruments less likely. It would also place the light source further from the retina than illumination devices placed through a pars plana incision, thereby reducing the chance of phototoxicity and increasing the allowable retinal surgical time. Various light sources can be incorporated including but not limited to LED light sources. If necessary and to avoid heat damage to the lens in phakic eyes, a heat insulating material (which may be transparent and/or translucent in some embodiments) can be incorporated into the posterior surface of the posterior ring, which being behind the iris will potentially make contact with the natural crystalline lens in a phakic eye.

In various embodiments, one or both of the outer border (s) of the posterior ring section and/or the anterior ring section (and/or various portions of the connecting segment of the central rim section) will desirably be flexible enough to allow folding of the device, while being rigid enough after unfolding of the device to stabilize the tissues of the peripheral iris against movement in a desired manner.

During a typical surgical procedure, the dilation device 10 can be prepared by rolling the device 10 into a deployment tool or injector, or the dilation device 10 can be supplied in a "ready to use" fashion (i.e., preloaded into an injector) on the surgical back table. Desirably, the dilation device 10 and associated injector tip will be sized and configured for insertion through a 2.0-2.2 mm incision in the eye, which is the size of incision used in phacoemulsifiation cataract surgery. Once injected into the anterior chamber of the eye and properly positioned and oriented, the dilation device 10 will desirably unroll and engage with the pupil. When fully unrolled and/or engaged to dilate the pupil, the anterior ring section 20 will desirably nearly completely "cover" an anterior surface of the iris 840, with the posterior ring section 30 positioned beneath the iris pupillary rim 850, which is desirably engaged within the cup 50 formed by the separation between the two disc sections, with these sections prevented from constriction by the central rim section which separates the two rings.

Desirably, engagement of the iris pupillary border (i.e., pupillary rim) will start with insertion and placement of a distal section of the posterior ring section to a location posterior to the pupillary border, and as the entire device unfolds in the eye and leaves the injector, a gentle posterior force can be applied by the surgeon to the device, which will desirably allow engagement of the remainder of the iris pupillary border with the dilation device 10 in a circumferential fashion—similar to replacing a tire on the rim of a bicycle wheel. Preferably, the entire process of injecting the dilation device 10 into the eye and deploying it such that it engages the pupillary border and dilates the pupil will desirably occur in a single continuous motion requiring only a single hand.

During the surgical procedure, the large positioning hole 70 (and/or other positioning holes 80) can be utilized to move and/or reorient the dilation device 10 as necessary. In addition, once the surgical procedure has been substantially completed, and/or when mechanical dilation of the iris is no longer necessary and/or desired, the dilation device 10 can be removed from the iris 840 by engaging the large positioning hole 70 on the anterior ring section 20 with an intraocular hook instrument (not shown). The anterior ring section 20 (specifically a portion thereof distal to the large positioning hole 70) can then be pulled towards the central iris and/or the main surgical incision, desirably causing the distal portion of the anterior ring section 20 (and attached portions of the device 10) to collapse and/or fold forward (i.e., anteriorly) in a "peeling" fashion, which desirably disengages the distal section of the device 10 (including a distal portion of the posterior ring section 30) from the iris pupillary margin. Further pulling on the intraocular hook will desirably progressively collapse and fold the dilation device 10 into the anterior chamber, desirably drawing the device 10 away from additional sections of the iris pupillary margin and towards the incision. As the dilation device 10 approaches and/or enters the incision, it will desirably fold as it enters the inner aspect of the surgical incision, which further reduces its profile and allows the dilation device to be pulled out of the anterior chamber.

In various alternative embodiments, other surgical tools such as forceps can be utilized to grasp a portion of the device 10, which will desirably cause a portion of the posterior ring section 30 to release from the pupillary rim. Where grasping of the anterior ring is desirous, particular care would desirably be exercised during this procedure to avoid engaging the iris with the surgical tool, which could result in damage to the iris sphincter.

Following extraction of the dilation device 10, and because the groove or cup 50 of the device distributes the dilation force uniformly across the pupillary rim, the use of the dilation device 10 and removal procedures thereof are less likely to result in sphincter tears and an irregular pupil than with use of other available dilation devices. Furthermore, the disclosed dilation device 10 and associated surgical procedures can be effectively utilized with both phakic and pseudophakic patients.

Figure 7:
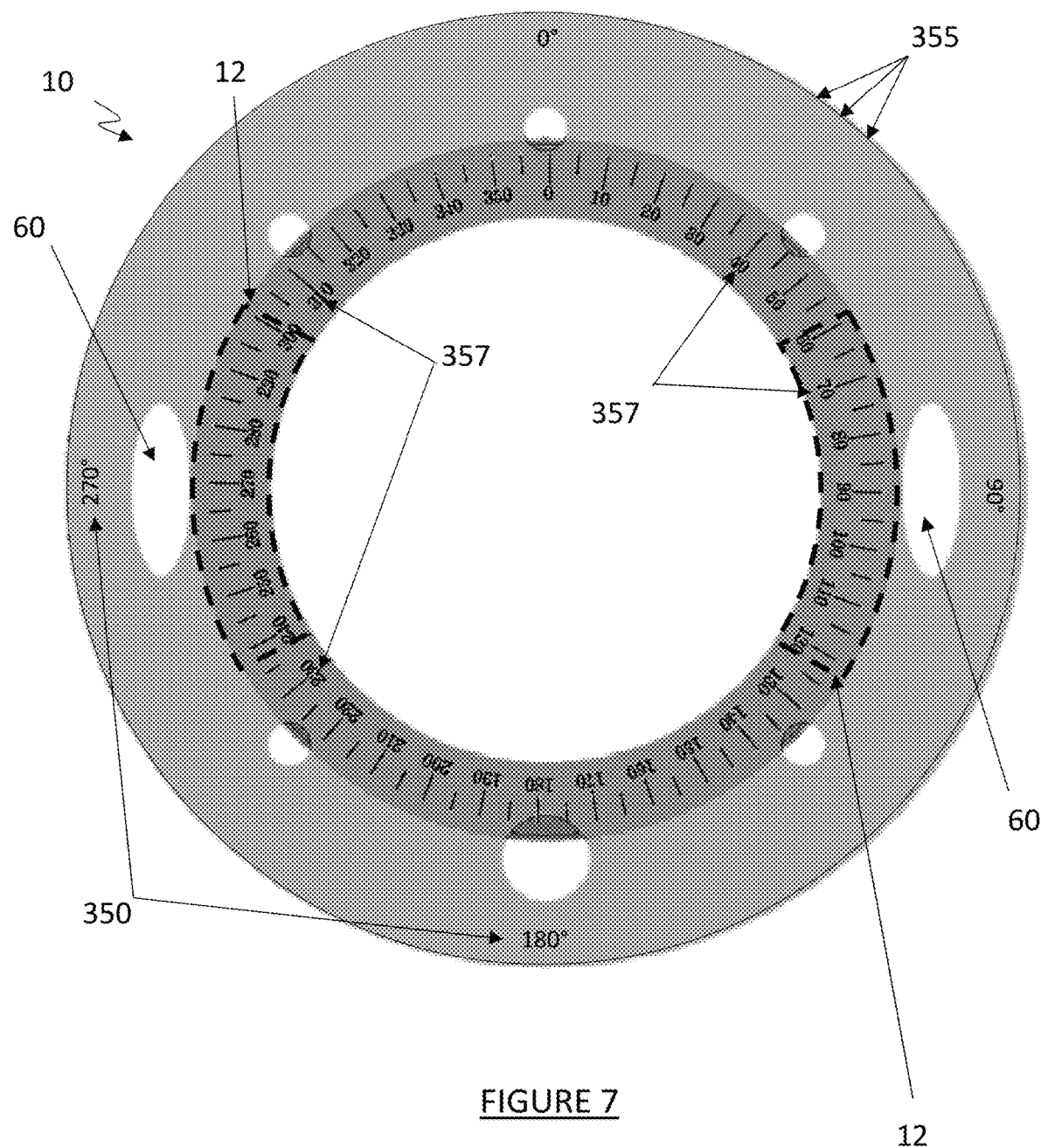
FIG. 7 depicts an alternative embodiment of a dilation device incorporating open arc portions on the posterior flange.
Figure 8:
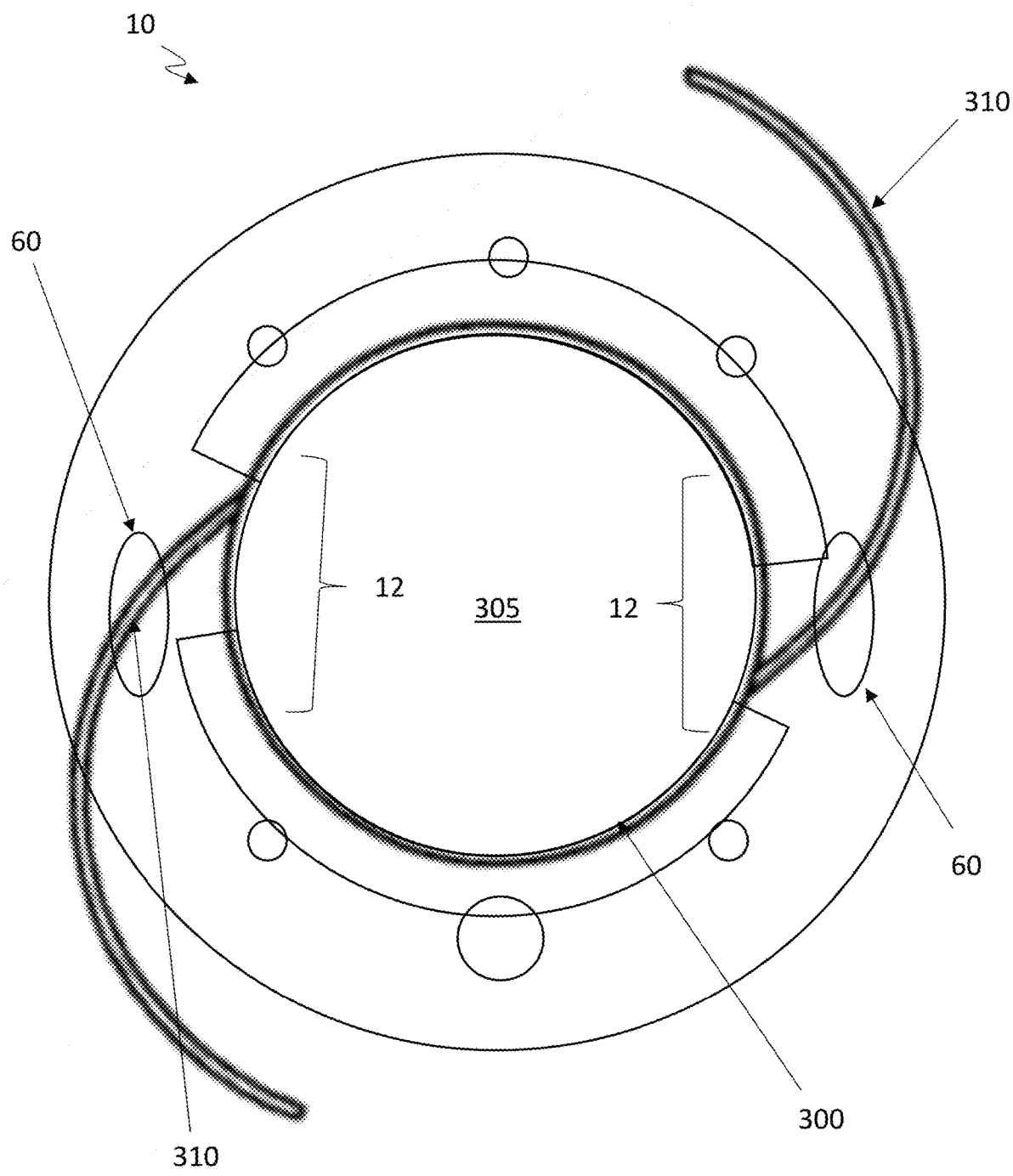
FIG. 8 depicts another alternative embodiment of a dilation device.

The various disclosed embodiments may be particularly useful during surgical procedures involving the implantation of an iris sutured intraocular lens in cases where the capsular bag of the crystalline lens (after removal of the cataract) is either unstable, damaged or absent such that the typical intra-capsular bag placement of the intraocular lens is not possible. If desired, one alternative embodiment of a dilation device 10 could include open arc notches, openings and/or discontinuities 12 on the posterior ring section 30, which could extend anteriorly and partially or fully into the central rim section. The device can be manufactured optionally with this feature present or a surgeon could utilize suture scissors to excise the 2 arcs or notches in the posterior ring section adjacent to the suture guide slits prior to injecting the ring into the eye, such as shown in FIGS. 7 and 8. These arc discontinuities, openings and/or notches could be positioned to allow capture and stabilization of intraocular lens haptics and/or also to allow the haptics to rest closer to the posterior iris surface (as opposed to being angled more posteriorly in cases when an intraocular lens optic is positioned over the ring structure for suture fixation of the haptics to the iris). For example, a 6.3 mm inner diameter of the anterior and posterior ring sections could be selected for the dilation device, to accommodate a flexible optic 6.5 mm diameter intraocular lens 300, which can be supported by the rim of the smaller diameter opening in the dilation ring device (which allows the slightly larger diameter of the optic of the intraocular lens to rest on the slightly smaller edge of the diameter of the central opening). This could potentially stabilize the entire IOL structure while the surgeon sutures the haptics to the iris using the suture guide slots 60 as a guide. Alternatively, a dilation device having a larger diameter opening could be utilized, if desired, but such a ring may be too large to completely support the lens in this desired manner.

FIG. 7 depicts one alternative embodiment of a dilation device 10 (view from anterior to the device), incorporating open arc portions on the posterior flange behind the plane of the anterior ring (dashed lines), and displaying degree markings present on the anterior surface of the anterior ring for use in facilitating rotational alignment of surgical implants, including toric intraocular lenses. The series of degree markings 350 and/or protractor markings 357 (i.e., 0 degrees to 360 degrees in various degree increments) could be provided and/or can be etched into an anterior/posterior side and/or top 355 of the anterior ring section to guide alignment of toric intraocular lens implants (and/or other implants), which could include markings that can facilitate rotational alignment of a toric intraocular lens implant when a toric intraocular lens is used. In one exemplary embodiment, hash marks and/or degree markings 357 can be provided at or near the inner and/or outer circumference of the of the larger anterior ring to facilitate such alignment or for other uses.

When used to facilitate iris suture fixation of an intraocular lens 300, a lens 300 can be desirably rotated so as to align the haptics 310 with the suture guide slits 60 and the open arc portions 12 of the posterior ring section, such as shown in the alternative embodiment of FIG. 8. In this Figure, alignment of an intraocular lens implant can be accomplished with the optic resting on and anterior to the rim of the anterior ring and the haptics behind the plane of the anterior ring and within the arcuate notches present in the posterior ring to guide the haptics into position posterior to the suture guide slits. Desirably, the haptics are positioned posteriorly to the iris (not shown) and aligned and stabilized by the open arcs 12, and can be sutured directly to the iris (using the suture guide slits to guide suture placement) with the dilation device in position, and the flexible optic 305 of the lens implant 300 can be pushed posteriorly through the internal opening of the dilation device 10 to rest posterior to the iris after the haptics are sutured to iris.

In various embodiments, the disclosed dilation devices could be used for a variety of purposes, including as scaffolding for additional intraocular device applications used during cataract and/or other procedures. The dilation device assembly can be constructed with additional fenestrations or other features for use with specific devices used in intraocular surgery and/or for the purpose of positioning and stabilizing these devices, including devices for creation of the anterior capsular opening during cataract surgery (capsulotomy devices) and/or capsular bag supports for example in phacoemulsification cataract surgery cases in which there is zonulysis and instability of the capsular bag and to permit successful completion of cataract extraction.

If desired, the dilation device 10 can be provided to a surgeon in a kit, containing a plurality of dilation devices of varying sizes and/or shapes, including multiple devices of varying sizes, shapes and/or configurations. In one exemplary embodiment, a plurality of distraction devices could be provided, each device having an anterior ring section that is made in progressively larger diameters, including devices having 8 mm, 9 mm, 10 mm, 11 mm, 12 mm, 13 mm, 14 mm, 15 mm, 16 mm, 17, mm and 18 mm (or larger, as required by patient anatomy). In special cases, the anterior ring section could be particularized for the patient anatomy, such as a distraction device of up to 16 mm or greater for use in buphthalmic eyes (i.e., in a person with congenital glaucoma).

In each of the anterior, posterior and/or central rim sections of the device 10, a series of openings, grooves and/or other features could be formed therein for a variety of purposes, some of which are primarily to facilitate fluid flow and/or provide alignment and/or guidance and/or access for a surgeon during the surgical procedure. For example, the anterior ring section 20 can includes two or more suture guide slits 60, which in the embodiment of FIG. 2 can comprise elongated or oval shaped openings of approximately 2 mm length by 1.2 mm width. (In various embodiments, two suture guide slits may be desirous, or in other alternative embodiments the ring can be constructed with fewer or additional slits as required for specific intraocular lenses used and/or other purposes). The anterior ring section 20 can alternatively include at least one large opening 70, which can comprise an opening of approximately 1.2 mm in diameter. In addition, a series of smaller openings 80 can be formed through the anterior ring section 20, each of these openings 80 being approximately 1 mm in diameter.

Figure 6:
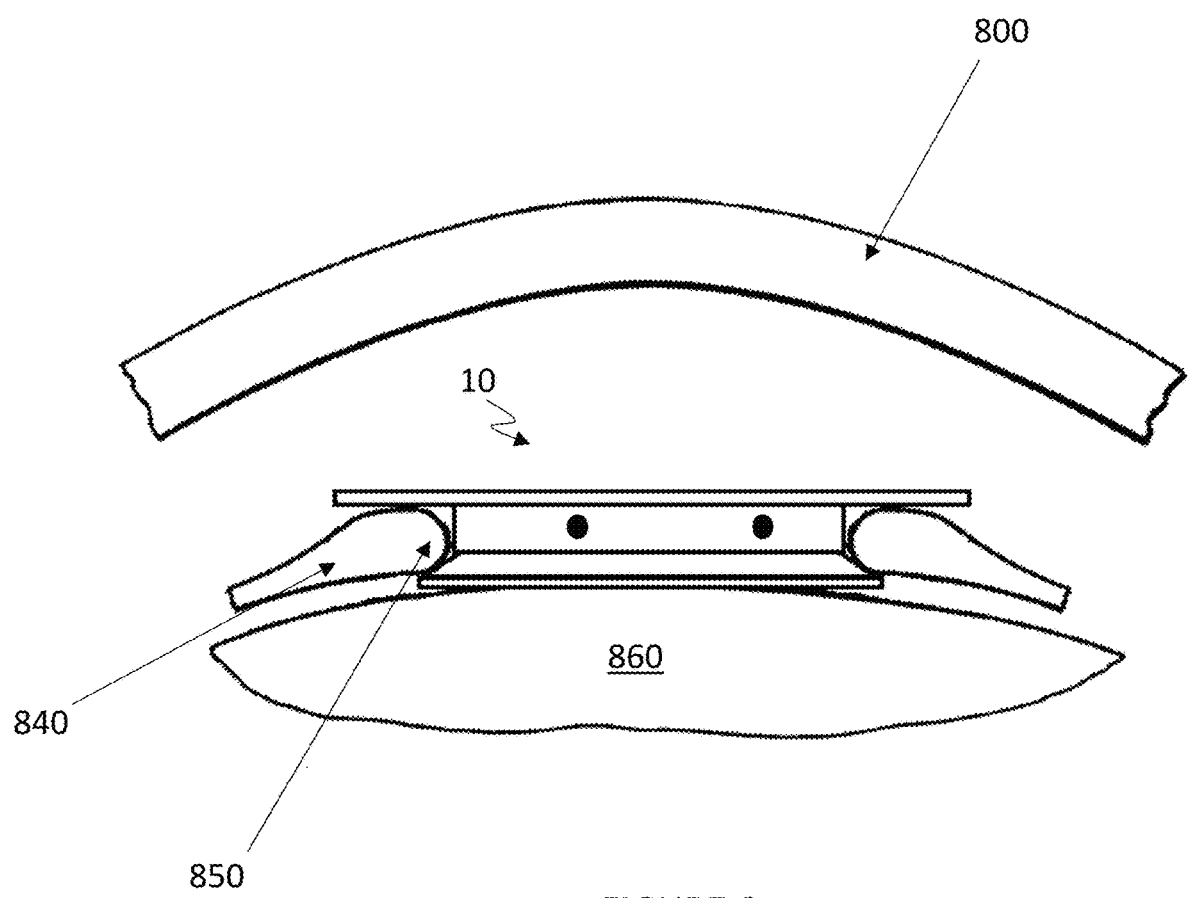
FIG. 6 depicts the embodiment of FIG. 2 during use in dilating a patient's iris.

To ensure flow of irrigation fluid between the space anterior to the ring 10 and crystalline lens of the patient 860 and the posterior segment space or chamber 820 behind the iris 840 and posterior ring 30 (when positioned to enlarge the pupil during surgery), it may be desirous to incorporate fenestrations or notches 90 in the device, placed full thickness through the central border ring 40 (which could also extend more posteriorly into the inner aspect of the posterior ring) or be present as partial antero-posterior thickness and/or full inner-outer diameter communicating thickness notches 450 in the posterior ring 30. Desirably, these openings will desirably maintain relatively equal fluid pressures between the anterior chamber 810 and posterior chamber 820 when the device is positioned to dilate the iris, such as shown in FIG. 6. When present in the central rim 40, the openings 90 will desirably range in width or diameter from 0.1 mm to 0.3 mm, with smaller sizes being preferred to reduce and/or limit disruption of the smooth surface of the central rim section 40 that desirably contacts the pupillary rim. Without flow fenestrations such as described herein, there is the potential of device-lens block, which can create hazardous hyper-deepening of the anterior chamber when the anterior chamber is pressurized with irrigation fluid. Desirably, full thickness openings can be provided in various locations of the distraction device to allow equilibration of pressure between the anterior and posterior chambers of the eye when the device is in position during surgery.

During surgery, various openings, notches and/or other "gaps" formed in the device could desirably allow circulation of irrigation fluid from the anterior chamber through the bypass openings to the area behind the iris and anterior to the lens of the eye, then back through the space between the lens of the eye and the smaller ring and into the anterior chamber through the central opening in the ring device. The effect would be to desirably equilibrate the pressure between the back of the iris and the front of the iris and prevent hyper-deepening of the anterior chamber when the anterior chamber is filled with irrigation fluid such as during cataract surgery.

In addition, the large opening 70 can facilitate positioning and/or handling of the dilation device 10, including rotation, removal and/or folding of the device 10 at the conclusion of the surgery. The suture guide slits 60 can function to facilitate alignment and/or suture fixation of intraocular lenses in complicated cataract surgery cases, where the lens may be sutured while the pupil dilation device remains in place, and the device can be subsequently removed without disturbing the lens implant.

In the disclosed embodiments, the continuous circular structure of both the anterior and/or posterior ring sections and the larger transparent or translucent anterior ring section desirably facilitate positioning of the dilation device 10 within the pupil with a continuous single maneuver, similar in concept to fitting a tire onto the rim of a bicycle wheel. In one exemplary embodiment, the smaller posterior ring section might desirably first engage the pupillary border at an edge diametrically opposite to the surgical incision from which the device is inserted into the eye. In this manner, unfolding and/or expansion of the device and the continuity of the posterior ring could allow the entire posterior ring to follow into position behind the pupillary border, while the pupillary border is stabilized by the larger anterior ring.

In various embodiments the continuity of the anterior and posterior ring sections desirably prevent "snagging" of the device by and during intraocular lens injection into the anterior chamber during cataract surgery, which may occur with other devices. Snagging of the dilation device by the intraocular lens during implantation or injection into the eye can cause tearing of the iris at its insertion into the ciliary body, which is undesirable.

In various embodiments, the smooth continuity of the rim joining the anterior and posterior ring sections desirably prevents and/or inhibits the occurrence of notching of the pupillary border, which can often occur with devices which make contact with the pupillary border at numerous individual points (i.e., 4 to 6 contact locations). Notching and/or other damage of the pupillary border can also occur at discrete locations with discontinuous iris devices, where there is greater stress on the iris border at the end of any gap in the device, such as at the end of a discontinuous ring, where the end makes contact with the iris border.

Moreover, the continuity of the larger anterior ring in the disclosed embodiments desirably provides improved stabilization for iris tissue during dilation and the surgical procedure, in that iris tissue should not herniate through the smaller openings in the ring. However, even if such herniation may occur, the amount of herniation should be extremely small, and desirably would not cause the dilation device to dislodge from the iris or iris tissue to herniate through the surgical incision. This may be especially important during a cataract surgery procedure in an eye suffering from IFIS, where the iris tissue typically follows any path of least resistance and will often herniate through the main cataract surgery incision as well as the paracentesis incision (and in similar fashion will tend to come forward through a "broken" expansion structure at one or more points of discontinuity).

Desirably, the smaller diameter of the posterior ring allows the posterior ring to be easily "pushed" through the pupil during placement to dilate the pupil. The width of the posterior ring will desirably be sufficient to rest behind the edge of the pupil and engage the iris pupillary border and prevent disengagement during surgery. Dilation is maintained by the continuous circular rim which joins the two flat anterior and posterior rings and connects to the inner rim of each ring, such that when the ring assembly is properly placed it sandwiches the pupillary border between the anterior and posterior rings. The outer border of the posterior ring may be sloped posteriorly in the radial direction with respect to the inner border to facilitate engagement of the pupillary border during insertion and the ring assembly can be made available with and without this feature.

Various embodiments of the presence invention include dilation devices that can provide a wide variety of advantages over existing dilation devices, including: (1) mechanically expanding a pupil in small pupil cases; (2) protecting the iris against prolapse in floppy iris cases and other cases where the iris may be prone to prolapse; (3) protecting the iris against instrument trauma and/or trauma from the phacoemulsification tip; (4) protecting the corneal endothelium by allowing phacoemulsification of cataract fragments to be performed directly over the iris plane and more posterior to and away from the corneal endothelium after the cataract is sectioned and sections are pulled out of the capsular bag—which will desirably make phacoemulsification safer in cases where in-bag phacoemulsification is currently avoided, such as eyes with zonulysis and resident (surgeon trainee) cases; (5) flattening of the anterior lens surface 862—see FIG. 1 (such as by contact with the posterior ring) when a steep central vault of the crystalline lens 860 presents, thereby preventing peripheral tears and/or guarding against peripheral capsulorrhexis tears (thereby making resident cases safer); (6) optionally providing axis and/or other markings on the dilating device, which facilitates alignment and/or placement of toric intraocular lens implants lenses used for correction of astigmatism; (7) facilitating the iris suture fixation of intraocular lens implants; (8) providing continuous, smooth dilation surfaces for contacting the iris, which are less likely to notch and/or damage the pupillary sphincter than currently available devices; (9) providing a dilation device suitable for use in cases of zonular instability, where the posterior ring can be inserted within a capsulorrhexis opening to hold the capsular bag in place (by supporting the anterior capsule during phacoemulsification), which will provide more uniform continuous support of the anterior capsule as compared to multiple single point support with the current best option capsular support hooks and/or (10) providing an intra-ocular examination and/or illumination device capable of self-alignment and/or fixation and which does not require additional surgical incisions for insertion and/or removal.

Because the dilation device 10 is desirably in direct physical contact with various eye structures while mechanically dilating the pupillary rim 850 and iris 840 of an eye, it is anticipated that biocompatible materials and/or biocompatible coatings will be incorporated into construction of the dilation device. Moreover, because folding and/or compacting of the device is desired during insertion into and/or removal from the eye through a surgical incision, the component materials will desirably be both flexible, to aid in insertion, and elastic, to provide the desired dilatory force to expand the iris. "Elastic", as the term is used herein, means the property of recovering to an original shape (or recovering some portion of the original shape) after deforming forces (i.e., folding and/or compacting) are removed.

Another significant advantage of the disclosed embodiments, including the large diameter of the anterior ring, is that the device protects the iris against trauma during insertion of a phacoemulsification tip, a feature which can be important during the training of novice surgeons. Another aspect which will provide greater safety during training of novice surgeons learning phacoemulsification is that lens material can be emulsified directly over the device as it lies over the iris, without fear of damaging the iris. In addition, by emulsifying lens material directly above the iris the phacoemulsification tip can be positioned farther from the corneal endothelium, offering greater protection to the endothelium from ultrasound energy then with current distraction devices.

Elastic materials possessing desirable characteristics for the dilation device could include a silicone or an organosilicone polymer sold under the name "Silastic" by Dow Corning. However, other suitable elastic or elastomeric materials exist that may be used including butyl rubbers, ethylene propylene diene terpolymer (EPDM), polysulfide rubber, silicone rubber, neoprene (polychloroprene), chlorsulfonated polyethylene, acrylonitrile-butadiene copolymer (nitrile rubber), styrene butadiene copolymer, acrylonitrile butadiene, copolymer-polyvinyl chloride polymer blends, polyisobutylene, polyepichlorohydrin, natural and synthetic polyisoprene, polyvinyl chloride-polybutadiene rubber, polyurethanes, fluorocarbon elastomers such as vinylidene, fluoride-chlorobifluorethylene copolymers, vinylidene-fluoride-hexafluorethylene copolymers, and fluoroacrylate elastomers, as well as many others.

Desirably, the anterior and/or posterior flanges or rings of the device (and optionally portions of the rim section) could comprise flexible materials and/or material supports having some degree of "shape memory" which could include the incorporation of external and/or internal scaffolding and/or a skeletal framework of shape memory materials.

In one exemplary embodiment, the dilation device could be machined or formed from existing silastic tubing, with the groove formed into an outer wall of the tubing and a posterior portion of the tubing reduced in outer diameter (i.e., to form the posterior flange). Alternatively, the dilation device 10 could be directly molded utilizing well known silicone or other material molding techniques, which can significantly eliminate any irregularities associated with tubing and/or machining thereof.

In various embodiments, a dilation device could incorporate preferred anterior flange dimensions of the anterior ring section (i.e., extending outward radially from the central rim section) ranging from about 0.5 mm to about 4.0 mm, while preferred radial dimensions of the posterior flange section could range from about 0.5 mm to about 2.0 mm. It should also be recognized by those skilled in the art that these are only preferred dimensions, and that ring/flange sizes outside of these ranges could fall within the principles of the present invention.

In various embodiments, the width of the cup or groove 50 of the pupillary dilation device 10 will desirably be approximately 0.5 mm, but could alternatively range from about 0.1 mm to about 0.7 mm, with an overall radial thickness of the rim section 40 being about 0.1 mm to 0.3 mm. If dilation device 10 is wider than this size, it might be more difficult to insert the device into the pupil, although such insertion may be acceptable for the principles of the present invention depending upon material construction and/or flexibility. Alternatively, if it is smaller than these sizes, the groove might be unable to properly accommodate and/or retain the pupillary rim a desired degree without potential for causing unwanted damage thereto (although smaller sized may be preferred for various patients having smaller anatomy).

The dilation device as disclosed has many applications. It is particularly useful in providing safe and reliable dilation of the pupil, thereby providing good visualization of the posterior pole and retina periphery during vitreoretinal surgery. However, it is also useful for dilating pupils that are unresponsive to pharmacologic agents, for preventing pupillary constriction during routine phacoemulsification, in cases where emergency dilation is needed such as intraoperative pupillary miosis during phacoemulsification and during "open sky" triple procedures to aid in visualization of lens removal, implantation and/or vitrectomy.

Figure 9:
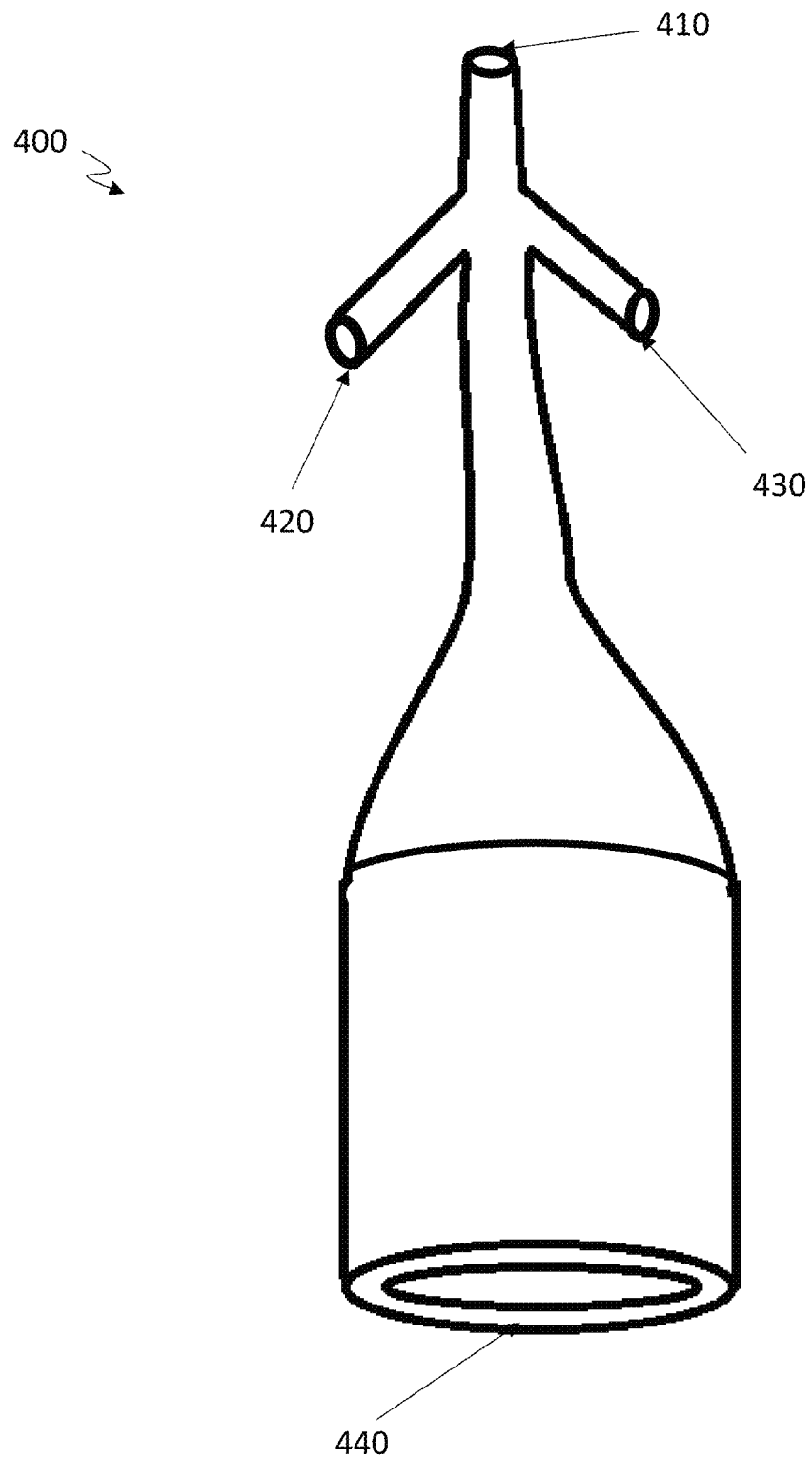
FIG. 9 depicts one embodiment of one exemplary embodiment of an irrigation sleeve.

FIG. 9 depicts one exemplary embodiment of an irrigation sleeve 400, which desirably provides improved control over the direction and/or degree of irrigation during the surgical procedure. The sleeve 400 can include an aspiration end lumen 410, from which a phaco needle (not shown) can extend, along with irrigation extensions 420 and 430, which can desirably divert flow fluid above the iris during cataract surgery (which will desirably provide additional protection against iris prolapse from the surgical incision by maintaining flow of irrigation fluid above the iris and preventing turbulent flow posterior to the iris) and a sleeve body 440, which can fit over the phacoemulsification tip of an ultrasonic surgical tool (not shown). Desirably, the sleeve body 440 of the irrigation direction regulator sleeve is sized and configured to be inserted over and/onto (and/or otherwise engageable with) the phacoemulsification tip in preparation for use for cataract surgery. The extensions of the irrigation sleeve 420 and 430 may be angled posteriorly with respect to the central tip to facilitate placement through a surgical incision.

Figure 10:
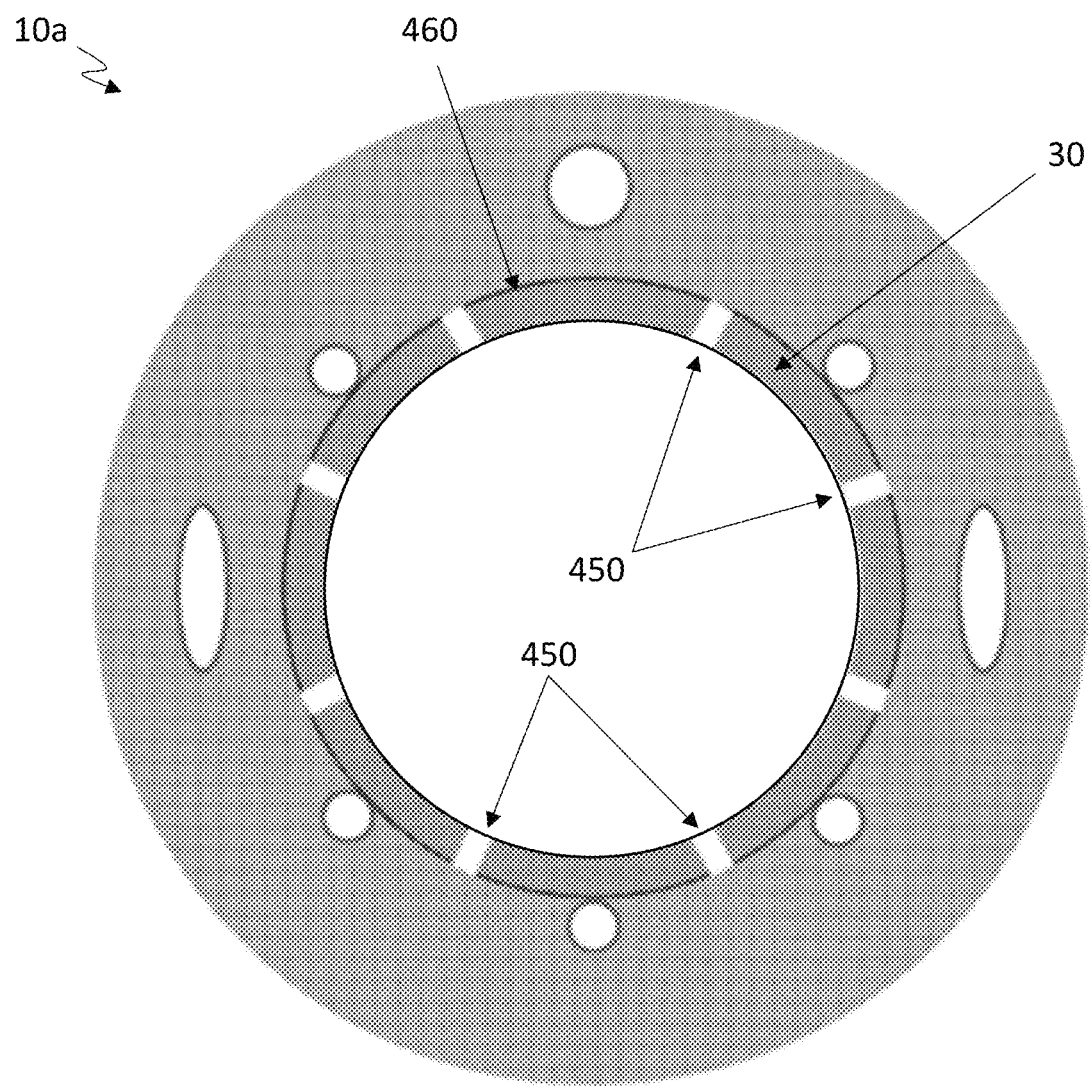
FIG. 10 depicts another alternative embodiment of a dilation device, incorporating partial cut-out sections on the posterior flange.

FIG. 10 depicts a posterior side view of one alternative embodiment of a distraction device 10a having many similar features to those previously described in accordance with various alternative embodiments. In this embodiment, the posterior ring section 30 includes partial notched or cut-out sections 450 (i.e., 8 sections in this embodiment, although other number and/or positioning of the sections is contemplated) with each of these notched or cut-out sections 450 allowing fluid flow between various areas of the posterior ring section 30 (i.e., allowing flow of surgical irrigation fluid along the depressed surface of the notch and/or from the space anterior to the device to the space posterior to the device), to allow for flow of fluid within the ring and/or between areas peripheral to the ring, so as to desirably equalize fluid pressure between various areas of the eye during surgery and/or prevent "lens-ring block" when irrigation fluid is flowing during cataract surgery. In this embodiment, the outer circumference 460 of the posterior ring section can include a black or shaded border to facilitate visualization when implanting into an eye and/or engaging the pupillary border.

Figure 11A:
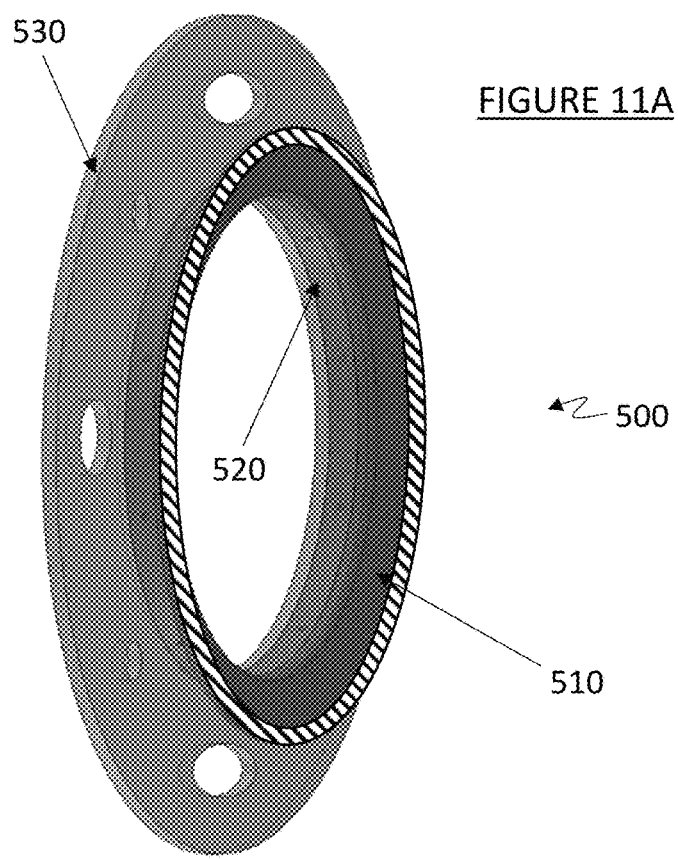
FIG. 11A depicts a perspective view of another alternative embodiment of a dilation device that incorporates illumination features.
Figure 11B:
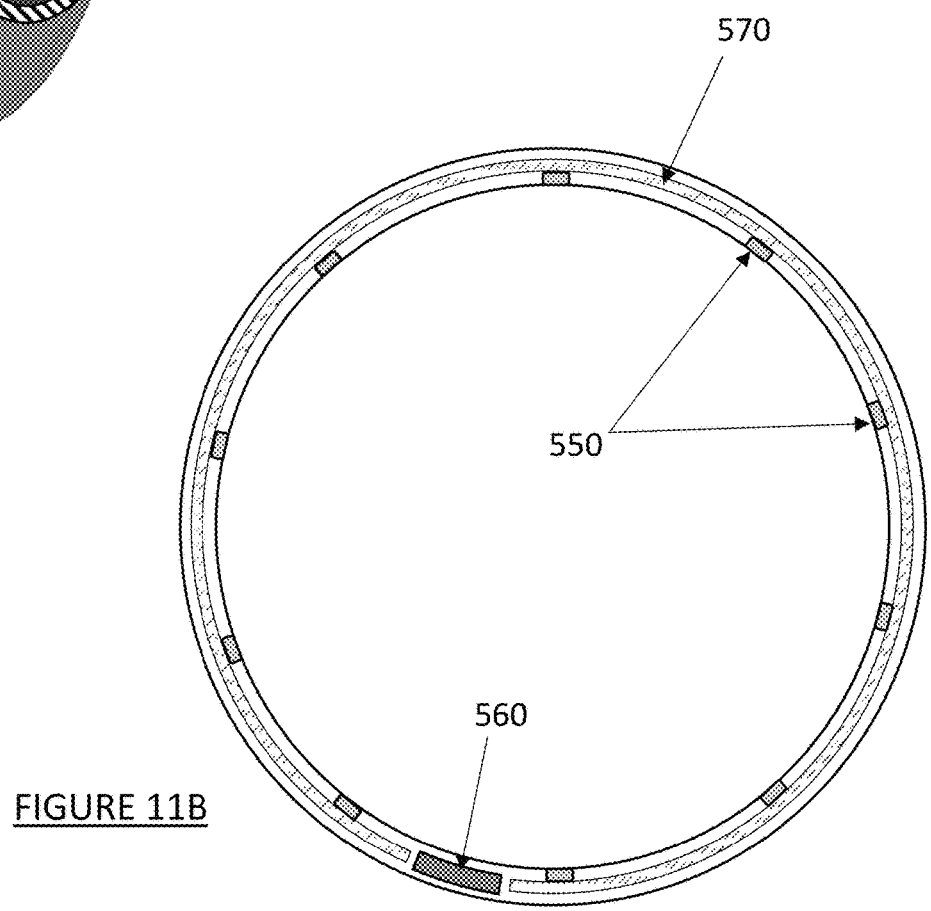
FIG. 11B depicts a top plan view of the illumination device of FIG. 11A.
Figure 12A:
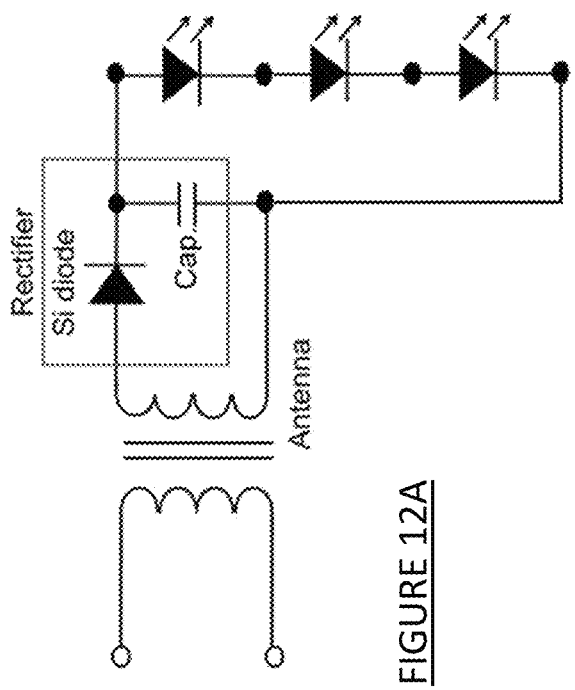
FIGS. 12A and 12B depict exemplary schematics of circuit diagrams for the device of FIG. 11A.
Figure 12B:
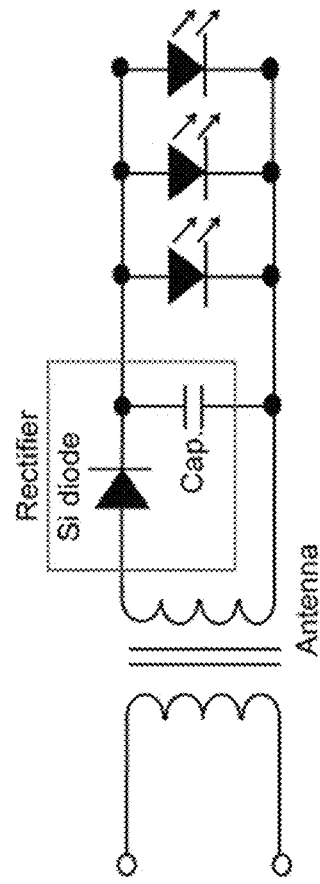
Figure 13:
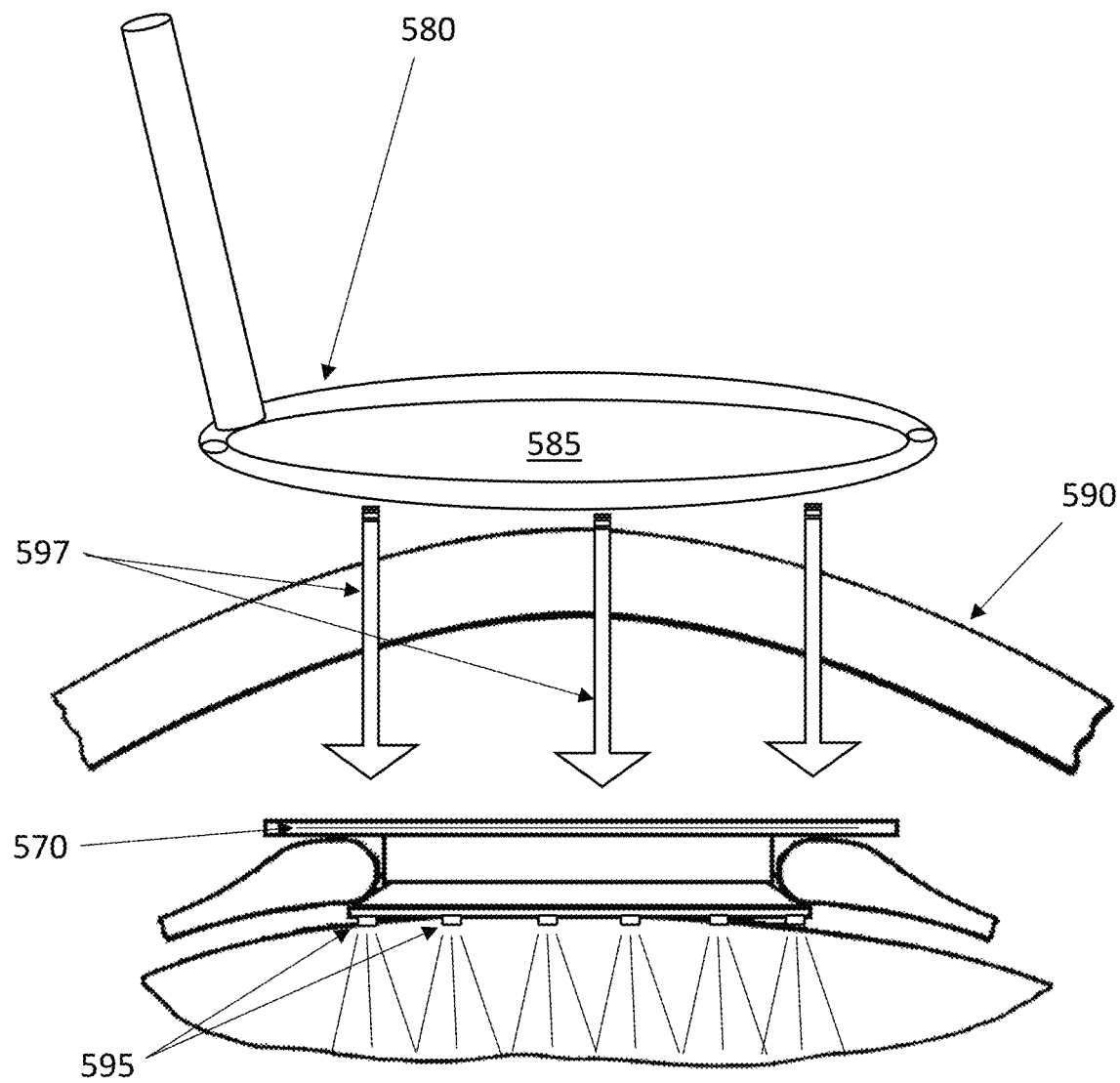
FIG. 13 depicts a side view of another alternative embodiment of a dilation device with illumination features positioned within an eye, with an associated RF energy transmission antenna positioned outside of the eye.

FIG. 11A depicts view of another alternative embodiment of a dilation device 500 that incorporates illumination features, which can desirably be utilized to facilitate visualization of interior eye structures (i.e., retinal illumination and/or other structures), such as during surgical procedures being performed within an eye. In this embodiment, the posterior ring 510 can incorporate an illumination source, such as LED light sources 550, which can be electrically connected (i.e., in parallel and/or series—see FIGS. 12A and 12B) to a current rectifier 560 and an inductive loop antenna 570, with the loop antenna being positioned on and/or encased within the structure of the device 500. Desirably, the loop antenna 570 could be deposed on/in the posterior ring 510 and/or on/in the central rim section 520 and/or on/in the anterior ring 530, or any combination thereof. As best seen in FIG. 13, once the dilation device 500 is positioned within an eye in a desired manner, an inductive power source antenna 580 can be positioned proximate to the outer surface 590 (i.e., cornea) of the eye, with wireless power 597 being transmitted (i.e., via an induced magnetic field or other wireless power transfer techniques) to the loop antenna 570 (depicted in FIG. 13 as encased within the anterior ring of the device) and illuminating the LED's 595 in a known manner. This LED illumination will desirably illuminate interior structures of the eye, which could include structures anterior to, proximal to, lateral to and/or anterior to the dilation device.

By providing power to the dilation device utilizing the disclosed inductive coil and/or similar devices, the level of illumination generated by the LEDs can be controlled externally (i.e., outside of the eye), which greatly simplifies the design and construction of the implanted device. This arrangement can also provide for external control of induced power levels and/or heat generation in/by the device, which may be monitored using a non-invasive optical temperature sensor, if desired. In addition, the employment of paired loop (or coils or other type) antennas in the present device allows for visualization and/or access by the surgeon through the open center 585 of the inductive power source antenna 580 (which is positioned proximate to an outer surface of the cornea) while also and allowing surgical access through the center of the inductive loop antenna 570 (which is contained within the dilation device currently dilating the iris within the eye).

It should be understood that a wide variety of wireless power transmission techniques and/or devices could potentially be utilized in the various components of the present invention, including inductive coupling, resonant inductive coupling, capacitive coupling and/or magnetodynamic coupling, as well as transmissive coupling such as radio waves, microwaves and light waves.

Figure 14:
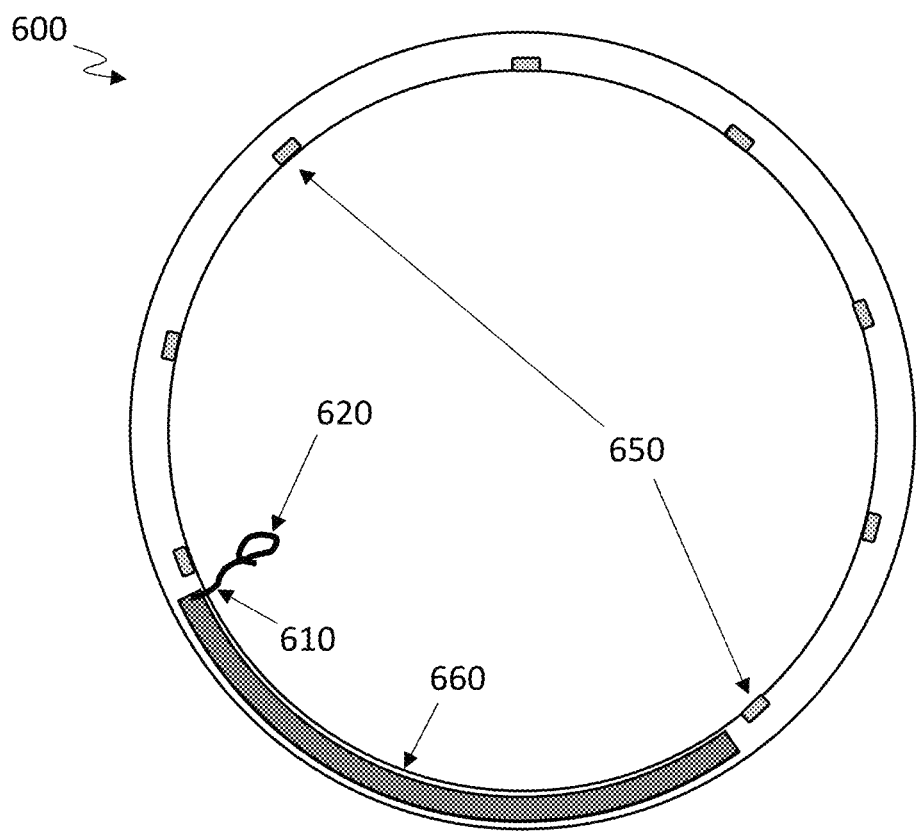
FIG. 14 depicts a top plan view of an alternative embodiment of a dilation device with illumination that incorporates an internal battery.

FIG. 14 depicts one alternative embodiment of a dilation device 600 which incorporates illumination features. In this embodiment, the posterior ring can incorporate an illumination source such as LED light sources 650 that are electrically connected to a battery 660 or other power source. Desirably, the device 600 will further include a switch or insulator 610, which desirably interrupts current flow to the LEDS prior to device implantation, and which can be activated once the device 600 has been properly positioned to dilate the iris within the eye. In the disclosed embodiment, the insulator 610 desirably includes a loop 620, which can be grasped and utilized (i.e., pulled) to activate the LED light sources (and possibly the insulator can be removed from the eye once activated) using a surgical hook or other appropriate tool.

By virtue of the foregoing, there is thus provided a pupillary dilation and protection device that may easily and quickly be inserted and removed, and that safely and reliably dilates the pupil without the complications experienced with the prior art demolitive or conservative measures. While the present invention has been illustrated by description of two embodiments, it is not the intention of the applicant to restrict or limit the scope of the appended claims to such detail. For example, the dilation device 10 could be formed with virtually any combination of one or more openings 60, 70, 80 and/or slots 12, 450, and still fall within the principles of the present invention. Additional advantages will readily appear to those skilled in the art; thus, the invention is not limited to the specific details, apparatus or method shown and described

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

What is claimed is:

1. A pupillary dilation and protection device comprising:
   a continuous biocompatible elastic ring having a receiver capable of receiving wirelessly transmitted energy, the continuous biocompatible elastic ring further having a radially outwardly extending annular anterior flange, a radially outwardly extending annular posterior flange and an interconnecting annular inner wall forming a generally U-shaped annular groove;
   said anterior flange at a first radial position having a radial dimension larger than a radial dimension of said posterior flange at the first radial position; and
   said posterior flange having an interior wall surface facing towards the anterior flange, the interior wall surface having a peripheral ridge portion and a central rim portion proximate to the interconnecting annular inner wall, the interior wall surface being tapered away from the anterior flange such that the central rim portion is closer to the anterior flange than the peripheral ridge portion;
   whereby when said continuous biocompatible elastic ring is inserted into the pupil of an eye, said groove engages and mechanically dilates the pupillary rim.

2. The pupillary dilation and protection device of claim 1 wherein said continuous biocompatible elastic ring is made from an organosilicone polymer.

3. The pupillary dilation device of claim 1 further comprising a centrally positioned first opening and a plurality of secondary openings formed completely through the anterior flange, at least two openings of the plurality of secondary openings positioned on opposing sides of the centrally positioned first opening.

4. The pupillary dilation device of claim 3, wherein the plurality of openings formed completely through the anterior flange comprise holes of a plurality of sizes.

5. The pupillary dilation device of claim 3, wherein the plurality of openings formed completely through the anterior flange comprise a pair of holes sized and configured for passing sutures therethrough.

6. The pupillary dilation device of claim 1, further comprising a plurality of openings formed completely through the interconnecting annular inner wall.

7. The pupillary dilation device of claim 1, further comprising a plurality of grooves formed into the interior wall surface of the posterior flange.

8. The pupillary dilation device of claim 1, further comprising a light source attached to the posterior flange.

9. The pupillary dilation device of claim 8, wherein the light source illuminates only a portion of a retina of the eye.

10. The pupillary dilation device of claim 8, wherein the light source comprises a light emitting diode filament.

11. The pupillary dilation device of claim 8, wherein the light source illuminates in a posterior direction of the eye.

12. The pupillary dilation and protection device of claim 1, wherein the inner diameter of said continuous biocompatible elastic ring is from about 5 mm to about 9 mm.

13. The pupillary dilation and protection device of claim 1, wherein the outer diameter of said continuous biocompatible elastic ring is from about 8 mm to about 16 mm.

14. The pupillary dilation and protection device of claim 1 wherein said annular U-shaped groove has an internal diameter of about 0.3 mm to about 1 mm.

15. The pupillary dilation and protection device of claim 1, wherein the interconnecting annular inner wall comprises a plurality of rim openings extending completely therethrough.

16. The pupillary dilation and protection device of claim 1, wherein the interconnecting annular inner wall comprises a plurality of notches formed in an inwardly facing surface thereof.

17. The pupillary dilation and protection device of claim 1, further comprising a pair of oval shaped openings formed through the anterior flange, at least a portion of the oval shaped openings being positioned radially outward of the posterior flange.

18. The pupillary dilation device of claim 1 further comprising a central opening and a plurality of secondary openings formed in the anterior flange, at least a portion of the plurality of secondary openings not being overlapped by the posterior flange.

19. The pupillary dilation device of claim 1, wherein the anterior flange can comprise a transparent flexible material.

20. The pupillary dilation device of claim 1, wherein the continuous biocompatible elastic ring incorporates a shape memory material imbedded therein.

* * * * *